(12) United States Patent
Firminger et al.

(10) Patent No.: US 8,249,887 B2
(45) Date of Patent: *Aug. 21, 2012

(54) PERSONALIZED PLAN DEVELOPMENT BASED ON IDENTIFICATION OF ONE OR MORE RELEVANT REPORTED ASPECTS

(75) Inventors: Shawn P. Firminger, Redmond, WA (US); Jason Garms, Redmond, WA (US); Roderick A. Hyde, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC

( * ) Notice: Subject to any disclaimer, the term of this patent is extended or adjusted under 35 U.S.C. 154(b) by 288 days.

This patent is subject to a terminal disclaimer.

(21) Appl. No.: 12/590,841

(22) Filed: Nov. 12, 2009

(65) Prior Publication Data

US 2011/0055105 A1 Mar. 3, 2011

Related U.S. Application Data

(63) Continuation-in-part of application No. 12/590,600, filed on Nov. 10, 2009, and a continuation-in-part of application No. 12/590,039, filed on Oct. 30, 2009, and a continuation-in-part of application No. 12/590,027, filed on Oct. 29, 2009, and a continuation-in-part of application No. 12/587,127, filed on Sep. 30, 2009, and a continuation-in-part of application No. 12/587,018, filed on Sep. 29, 2009, and a continuation-in-part of application No. 12/584,653, filed on Sep. 8, 2009, and a continuation-in-part of application No. 12/584,489, filed on Sep. 3, 2009.

(51) Int. Cl.
*G06Q 10/00* (2012.01)
(52) U.S. Cl. .......................................... 705/1.1
(58) Field of Classification Search .................... 705/1.1
See application file for complete search history.

(56) References Cited

U.S. PATENT DOCUMENTS 4,853,854 A 8/1989 Behar et al.
(Continued)

OTHER PUBLICATIONS

Chen, Jason; "You Can Soon Track Your Heart Rate with Your iPhone"; Gizmodo; Bearing a date of Oct. 9, 2009; p. I; Creative Commons License; located at: http://gizmodo.com/5378340/you-can-soon-track-your-heart-rate-with-your-iphone; printed on Oct. 29, 2009.

(Continued)

*Primary Examiner* — Jonathan Ouellette

(57) ABSTRACT

A computationally implemented method includes, but is not limited to: identifying one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes; and developing one or more personalized plans designed to facilitate an end user to achieve the one or more target outcomes when one or more emulatable aspects indicated by the one or more personalized plans are emulated, the development of the one or more personalized plans being based, at least in part, on the identifying In addition to the foregoing, other method aspects are described in the claims, drawings, and text forming a part of the present disclosure.

44 Claims, 20 Drawing Sheets

U.S. PATENT DOCUMENTS

| | | | |
|---|---|---|---|
| 5,961,446 | A | 10/1999 | Beller et al. |
| 6,338,044 | B1 | 1/2002 | Cook et al. |
| 6,353,447 | B1 | 3/2002 | Truluck et al. |
| 6,842,604 | B1 | 1/2005 | Cook et al. |
| 7,587,368 | B2 | 9/2009 | Felsher |
| 7,668,735 | B2 | 2/2010 | Grace et al. |
| 7,702,685 | B2 | 4/2010 | Shrufi et al. |
| 7,860,852 | B2 | 12/2010 | Brunner et al. |
| 7,908,182 | B1 | 3/2011 | Gupta |
| 7,959,567 | B2 | 6/2011 | Stivoric et al. |
| 8,005,906 | B2 | 8/2011 | Hayashi et al. |
| 2002/0107707 | A1 | 8/2002 | Naparstek et al. |
| 2004/0015337 | A1* | 1/2004 | Thomas et al. ............... 703/11 |
| 2005/0197553 | A1 | 9/2005 | Cooper |
| 2005/0216300 | A1 | 9/2005 | Appelman et al. |
| 2006/0036619 | A1* | 2/2006 | Fuerst et al. ............... 707/100 |
| 2007/0088576 | A1 | 4/2007 | de Beus et al. |
| 2008/0091471 | A1 | 4/2008 | Michon et al. |
| 2008/0288425 | A1* | 11/2008 | Posse et al. ............... 706/12 |
| 2008/0294012 | A1* | 11/2008 | Kurtz et al. ............... 600/300 |
| 2009/0044113 | A1 | 2/2009 | Jones et al. |
| 2009/0070679 | A1 | 3/2009 | Shen et al. |
| 2009/0075242 | A1 | 3/2009 | Schwarzberg et al. |
| 2009/0076335 | A1 | 3/2009 | Schwarzberg et al. |
| 2009/0100469 | A1 | 4/2009 | Conradt et al. |
| 2009/0176526 | A1* | 7/2009 | Altman ............... 455/556.1 |
| 2009/0258710 | A1* | 10/2009 | Quatrochi et al. ............... 463/43 |
| 2009/0271247 | A1 | 10/2009 | Karelin et al. |
| 2009/0292814 | A1 | 11/2009 | Ting et al. |
| 2009/0299990 | A1* | 12/2009 | Setlur et al. ............... 707/5 |
| 2009/0313041 | A1* | 12/2009 | Eder ............... 705/2 |
| 2009/0319288 | A1 | 12/2009 | Slaney et al. |
| 2009/0326981 | A1* | 12/2009 | Karkanias et al. ............... 705/3 |
| 2010/0063993 | A1* | 3/2010 | Higgins et al. ............... 709/203 |
| 2010/0114788 | A1 | 5/2010 | White et al. |
| 2010/0268830 | A1 | 10/2010 | McKee et al. |
| 2010/0281364 | A1* | 11/2010 | Sidman ............... 715/713 |
| 2010/0293247 | A1 | 11/2010 | McKee et al. |
| 2010/0305806 | A1* | 12/2010 | Hawley ............... 701/33 |
| 2011/0022602 | A1 | 1/2011 | Luo et al. |
| 2011/0179161 | A1 | 7/2011 | Guy et al. |
| 2011/0185020 | A1 | 7/2011 | Ramamurthy et al. |
| 2011/0252101 | A1* | 10/2011 | Davis et al. ............... 709/206 |

OTHER PUBLICATIONS

"Fitbit"; Bearing a date of 2009; pp. 1-2; Fitbit, Inc., located at: http://www.fitbit.com; printed on Oct. 29, 2009.

"Free Exercise Programs—Workout Routines & Weight Loss Diet Plans"; Freetrainers.com; Bearing dates of 2000-2008; pp. 1-2; located at: http://www.freetrainers.com/FT/jsp/index.jsp; printed on Sep. 2, 2009.

Wilson, Mark; "Philips DirectLife Turns Exercise Into a Status Bar"; Gizmodo; Bearing a date of Oct. 21, 2009; pp. 1-2; Creative Commons License; located at: http://gizmodo.com/5386577/philips-directlife-turns-exercise-into-a-status-bar; printed on Oct. 29, 2009.

"Your Personalized Development Plan"; Central Michigan University; Bearing a date of 2004; p. 1; located at: http://www.chsbs.cmich.edu/leader_model/dplanintro.htm; printed on Sep. 2, 2009.

U.S. Appl. No. 12/655,582, Firminger et al.
U.S. Appl. No. 12/655,581, Firminger et al.
U.S. Appl. No. 12/655,365, Firminger et al.
U.S. Appl. No. 12/655,250, Firminger et al.
U.S. Appl. No. 12/655,075, Firminger et al.
U.S. Appl. No. 12/653,972, Firminger et al.
U.S. Appl. No. 12/653,387, Firminger et al.
U.S. Appl. No. 12/653,386, Firminger et al.
U.S. Appl. No. 12/653,180, Firminger et al.
U.S. Appl. No. 12/653,117, Firminger et al.
U.S. Appl. No. 12/592,946, Firminger et al.
U.S. Appl. No. 12/592,944, Firminger et al.
U.S. Appl. No. 12/592,548, Firminger et al.
U.S. Appl. No. 12/592,544, Firminger et al.
U.S. Appl. No. 12/592,161, Firminger et al.
U.S. Appl. No. 12/592,075, Firminger et al.
U.S. Appl. No. 12/590,600, Firminger et al.
U.S. Appl. No. 12/590,039, Firminger et al.
U.S. Appl. No. 12/590,027, Firminger et al.
U.S. Appl. No. 12/587,127, Firminger et al.
U.S. Appl. No. 12/587,018, Firminger et al.
U.S. Appl. No. 12/584,653, Firminger et al.
U.S. Appl. No. 12/584,489, Firminger et al.

Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the...; printed on Nov. 25, 2009.

"Exercise Pro Software Active Care Version 5"; BioEX Systems, Inc.; bearing dates of 1995-2009; pp. 1-4; located http://www.bioexsystems.com/ActiveCare.htm; printed on Dec. 17, 2009.

Gross, Daniel; "A Jewish Mother in Your Cell Phone"; Slate; bearing a date of Nov. 10, 2009; pp. 1-3; located at http://www.slate.com/formatdynamics/CleanPrintProxy.aspx?125919...; printed on Nov. 25, 2009.

Guez, Tomer; "Weight Loss Software, Food Diary, Exercise Tracker, and Medical Diary. 'The Food and Exercise Diary Software Version 6.0'"; bearing a date of Sep. 2009; pp. 1-17; located at http://www.weightlosssoftware.com/?ti=135&wn=2; printed on Dec. 17, 2009.

"Nutrition tracking software is critical for learning about foods and planning meals"; NutriCoach; bearing a date of Mar. 29, 2006; 6 total pgs.; located at http://www.nutricoach.net/diet_software.html; printed on Dec. 17, 2009.

"Nutritionmaker Focus Nutrition Software Motivate—Analyze—Instruct"; BioEX Systems, Inc.; bearing dates of 1995-2009; pp. 1-4; located at http://www.bioexsystems.com/NutritionMakerChiro.htm; printed on Dec. 17, 2009.

"Tired of a stiff neck and shoulders? Ergo Pro Computer Fatigue Software reminds you when to stretch and shows you how"; BioEX Systems, Inc.; bearing dates of 1995-2009; pp. 1-3; located at http://www.bioexsystems.com/ExerciseBreak.htm; printed on Dec. 17, 2009.

"VHI PC-Kits Desktop Edition"; Visual Health Information; pp. 1-2; located at http://www.vhikits.com/products/software/PCKitsDesktop.aspx; printed on Dec. 17, 2009.

Agger, Michael;"Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.

"Self-tracking links to get you started"; The Quantified Self: self knowledge through numbers; printed on Dec. 10, 2010; pp. 1-5; located at: http://quantifiedself.com/self-tracking-links-to-get-you-started/.

Gaonkar, Shravan, et al.; "Micro-Blog: Sharing and Querying Content Through Mobile Phones and Social Participation"; MobiSys '08; Jun. 17-20, 2008; pp. 174-186; ACM.

* cited by examiner

PERSONALIZED PLAN DEVELOPMENT BASED ON IDENTIFICATION OF ONE OR MORE RELEVANT REPORTED ASPECTS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/584,489, entitled PERSONALIZED PLAN DEVELOPMENT, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 3 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/584,653, entitled PERSONALIZED PLAN DEVELOPMENT, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 8 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,018, entitled PERSONALIZED PLAN DEVELOPMENT BASED ON OUTCOME IDENTIFICATION, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 29 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,127, entitled PERSONALIZED PLAN DEVELOPMENT BASED ON OUTCOME IDENTIFICATION, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 30 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,600, entitled PERSONALIZED PLAN DEVELOPMENT BASED ON IDENTIFICATION OF ONE OR MORE RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr, as inventors, filed 10 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,027, entitled PERSONALIZED PLAN DEVELOPMENT BASED ON ONE OR MORE REPORTED ASPECTS' ASSOCIATION WITH ONE OR MORE SOURCE USERS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr, as inventors, filed 29 Oct. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,039, entitled PERSONALIZED PLAN DEVELOPMENT BASED ON ONE OR MORE REPORTED ASPECTS' ASSOCIATION WITH ONE OR MORE SOURCE USERS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr, as inventors, filed 30 Oct. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A computationally implemented method includes, but is not limited to identifying one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes; and developing one or more personalized plans designed to facilitate an end user to achieve the one or more target outcomes when one or more emulatable aspects indicated by the one or more personalized plans are emulated, the development of the one or more personalized plans being based, at least in part, on the identifying. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for identifying one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes; and means for developing one or more personalized plans designed to facilitate an end user to achieve the one or more target outcomes when one or more emulatable aspects indicated by the one or more personalized plans are emulated, the development of the one or more personalized plans being based, at least in part, on the identifying. In addition to the foregoing, other system aspects are described in the claims, drawings, and text forming a part of the present disclosure.

A computationally implemented system includes, but is not limited to: circuitry for identifying one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes; and circuitry for developing one or more personalized plans designed to facilitate an end user to achieve the one or more target outcomes when one or more emulatable aspects indicated by the one or more personalized plans are emulated, the development of the one or more personalized plans being based, at least in part, on the identifying. In addition to the foregoing, other system aspects are described in the claims, drawings, and text forming a part of the present disclosure.

A computer program product including a signal-bearing medium bearing one or more instructions for identifying one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes; and one or more instructions for developing one or more personalized plans designed to facilitate an end user to achieve the one or more target outcomes when one or more emulatable aspects indicated by the one or more personalized plans are emulated, the development of the one or more personalized plans being based, at least in part, on the identifying. In addition to the foregoing, other computer program product aspects are described in the claims, drawings, and text forming a part of the present disclosure.

A method for developing one or more personalized plans that includes identifying, using a processor, one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes; and developing one or more personalized plans designed to facilitate an end user to achieve the one or more target outcomes when one or more emulatable aspects indicated by the one or more personalized plans are emulated, the development of the one or more personalized plans being based, at least in part, on the identifying.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
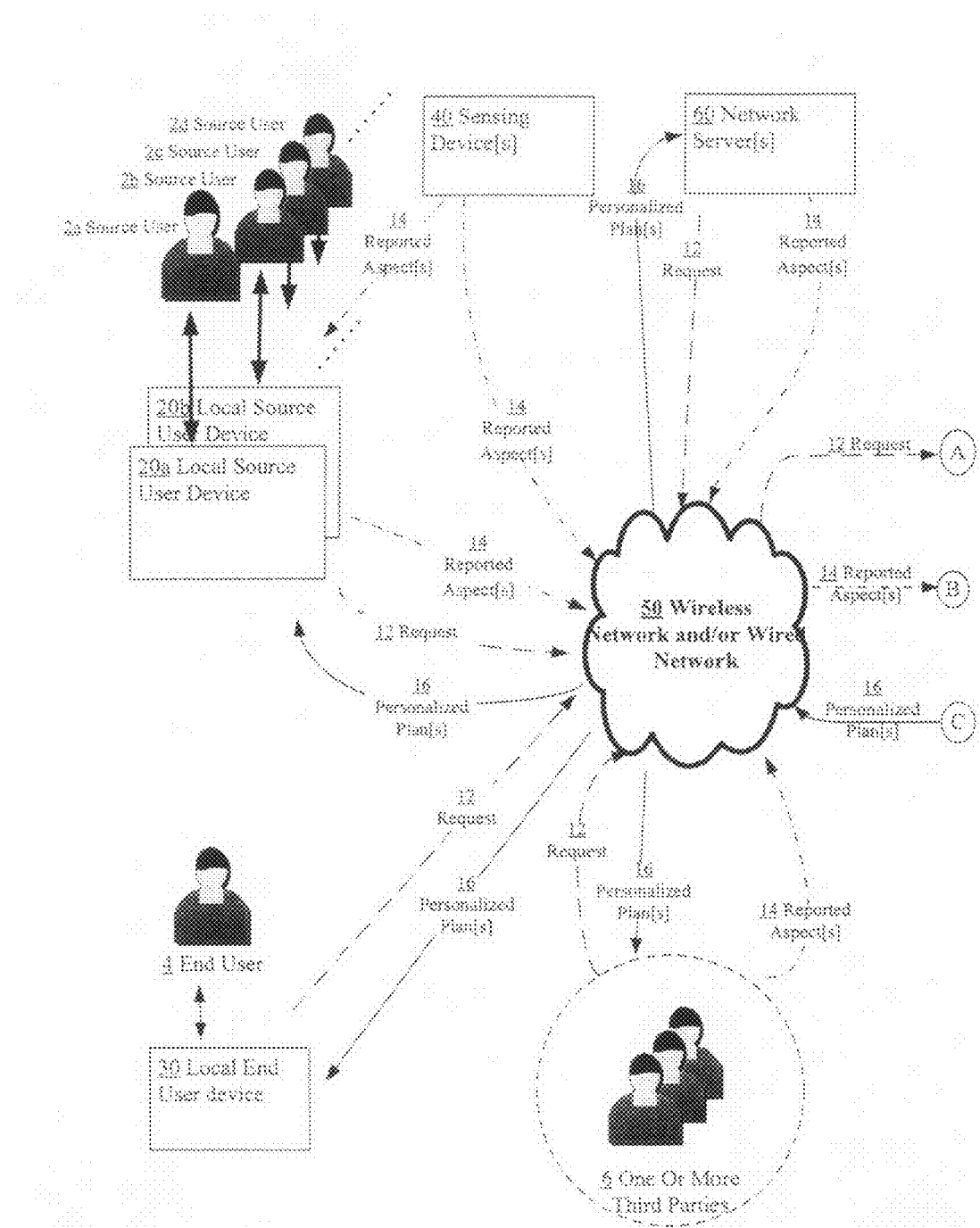
FIGS. 1a and 1b show a high-level block diagram of a Computing Device 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that has enjoyed explosive popularity in the computing/communication field is to electronically record one's daily activities, behaviors, thoughts, beliefs, traits, physical or mental states, physical characteristics, and other aspects of the person's everyday life onto an open journal. One place where such open journals are maintained is at social networking sites commonly known as "blogs" where one or more users may report or post every aspect of their daily lives. In brief, an "aspect," as will be referred to herein, may be in reference to any particular act, behavior, characteristic, user state or status, belief, and so forth, that may be associated with a user (e.g., a person including, for example, a network user such as a blogger or a social networking user). The process of reporting or posting blog entries is commonly referred to as "blogging." A newer type of blogging that has become very popular in recent times is microblogging, otherwise known as "twittering" or "tweeting." In microblogging, each of the microblogs that are posted are typically relatively short posts or entries, usually not more than 140 characters long.

Other types of social networking sites may also allow users to maintain open journals and to allow users to easily update their personal information. Such updates are typically made via, for example, social networking status reports otherwise known simply as "status reports." These social networking sites allow a user to report or post for others to view the latest status or other aspects related to the user.

Another recent tread in social networking is to employ one or more sensors to detect and report on a wide variety of aspects associated with users. Examples of sensors that may be used for such purposes vary widely, ranging from traditional devices that can detect and report on physiological parameters such as heart rate or blood pressure, to sensors that can detect certain user behaviors or activities such as toilet usage. Although a wealth of personal information provided through log entries (e.g., microblogs, status reports, sensor data, and so forth) are now available through these social networking sites, it is only recently has there been any effort to exploit such potentially useful data.

In various embodiments, methods, systems, circuitry, and computer program products are provided for developing, among other things, one or more personalized plans designed to facilitate an end user to achieve one or more target outcomes when one or more emulatable aspects indicated by the one or more personalized plans are emulated. In particular, the methods, systems, circuitry, and computer program products may be designed to identify (e.g., determine or find) one or more relevant reported aspects associated with one or more source users that are relevant to achieving the one or more target outcomes, the identification based at least in part on the one or more relevant reported aspects' relevancy with respect to the one or more target outcomes. Based on the identification of the one or more relevant reported aspects, the one or more personalized plans may then be developed by including into the one or more personalized plans the one or more emulatable aspects that may correspond to the one or more relevant reported aspects. The methods, systems, circuitry, and computer program products may be implemented by a variety of computing/communication devices including, for example, by a network device such as a server (e.g., network servers) or a local client device.

In some embodiments, the methods, systems, circuitry, and computer program products may be employed in order to, for example, identify from a large (or small) quantity of data that may indicate a plurality of reported aspects associated with one or more source users one or more reported aspects that may be relevant to achieving one or more target outcomes. For these embodiments, the large quantity of data to be examined may include data that indicate both relevant and non-relevant reported aspects (e.g., not relevant to achieving the one or more target outcomes) that are associated with one, few, or many source users.

As will be described herein, an "aspect" may be any behavior, act, belief, characteristic, state, and so forth associated with a particular person (i.e., a source user). A "reported aspect" may be any aspect associated with the person that has been reported. In some embodiments, a reported aspect may have been originally reported via log entries such as blog or microblog entries, status reports, journal entries, sensing device entries, and so forth. In some cases, a reported aspect may be at least originally reported by the source user that the reported aspect is associated with, by a sensing device that detects the aspect to be reported, or by a third party (e.g., another source user who may be reporting on an aspect of the first source user).

The determination of whether a reported aspect is relevant for achieving a particular target outcome (e.g., goal) may be based on one or more factors including one or more "relevancy factors." For example, in some embodiments, a reported aspect may only be relevant for achieving a particular target outcome only if the reported aspect is associated with a source user who has achieved the target outcome. That is, reported aspects that are associated with a source user who has not achieved the target outcome will most likely not be relevant to the achievement of the target outcome. Instead, only reported aspects that are associated with a "successful" source user (e.g., a source user who has achieved the target outcome) may be relevant to the achievement of the target outcome. And even if a reported aspect is determined to be associated with a source user who has achieved the target outcome, such a reported aspect may not necessarily be relevant as many, if not most, reported aspects that are associated with the source user may be completely immaterial to the achievement of the target outcome.

Thus, other factors such as "relevancy factors" may be considered when determining whether a particular reported aspect that is associated with a source user who has achieved the target outcome is actually relevant to the achievement of the target outcomes. Such relevancy factors may include, for example, whether the reported aspect associated with the successful source user indicates an aspect that occurred proximate to the achievement of the target outcome by the successful source user. That is, reported aspects associated with the successful source user that indicate aspects that occurred well before or well after the achievement of the target outcome by the successful source user may not have any bearing or relationship (e.g., causal relationship) with respect to the achievement of the target outcome.

For example, suppose an end user is interested in losing at least 20 pounds of body weight in two months (e.g., target outcome). Suppose further that a particular source user such as a microblogger has been determined to have lost 25 pounds of body weight in two months. In determining which reported aspects (e.g., dietary behavior, exercise activities, sleep activities, study activities, and so forth) associated with the source user may be relevant to achieving the target outcome, those reported aspects that indicate aspects (e.g., exercise activities) of the source user that occurred well before (e.g., one year before) the occurrence or achievement of the target outcome (e.g., 25 pound body weight loss in two months) by the source user will likely be considered not relevant.

Other relevancy factors may also be considered in determining whether a reported aspect is relevant to the achievement of the target outcome. For example, determining whether the reported aspect belong to an aspect type that is of interest to the end user. Suppose, for example, the end user in the above example believes that the key to losing weight is to have a good night's sleep. In that case, only reported aspects that relate to, for example, the sleep activities of the successful source user may be considered as being relevant. In some cases, the successful source user may also indicate what aspects or types of aspects associated with the source user may have contributed to his achievement of the target outcome. In such cases, only those reported aspects associated with the successful source user and that belong to the types of aspects that the successful source user considers relevant to achieving the target outcome may be considered as a relevant reported aspect. In still other cases, the relevancy of a reported aspect may be based on indications provided by one or more third party sources such as other source users (e.g., those who may not have achieved the target outcome), other end users, publications, medical research, and so forth, that may indicate the types of aspects that may be relevant to achieving the target outcome.

In any event, based at least in part on the identification of the one or more relevant reported aspects, one or more personalized plans may be developed that are designed to facilitate the end user to achieve the one or more target outcomes when one or more emulatable aspects included in the one or more personalized plans are emulated. In some embodiments, the development of the one or more personalized plans may be prompted when, for example, a request (e.g., a query, a command, a solicitation, and so forth) is received that may identify at least one of the one or more target outcomes. For these embodiments, the request may originate from an end user, a source user, a third party (e.g., a network service provider, a content provider, and so forth), or from some other origin.

A personalized plan may merely be a collection of one or more emulatable aspects. An emulatable aspect may be an indication of any behavior, act, trait, physical state, mental state, social state, declaration, belief, or any other facet of a person (i.e., source user) that may be emulated in order to achieve one or more target outcomes. In some cases, a personalized plan may include only a single emulatable aspect. For example, a personalized plan for reducing cavities (e.g., target outcome) may include a single emulatable aspect (e.g., avoid sweet desserts). In other cases, a personalized plan may include multiple emulatable aspects. For example, a personalized plan to lose 20 pounds of body weight (e.g., target outcome) may include multiple emulatable aspects (e.g., the personalized plan includes a schedule of swimming and jogging activities where each activity is an emulatable aspect). In cases where a personalized plan includes multiple emulatable aspects, the personalized plan may or may not define a relationship or relationships (e.g., temporal, specific time, or spatial relationships) between the multiple emulatable aspects included in the personalized plan. For instance, in the above weight loss example, the personalized plan may indicate when certain activities should be executed with respect to other activities (e.g., swimming on day one, jogging on day two, and so forth).

In some cases, a personalized plan may also indicate one or more emulatable intermediate outcomes that may be associated with one or more target outcomes of the personalized plan. For example, if a personalized plan includes a plurality of emulatable aspects, then one or more emulatable intermediate outcomes may also be included in the personalized plan that may represent one or more outcomes that are preferably or ideally achieved while the personalized plan is being executed and before the target outcome is achieved. In some cases, the emulatable intermediate outcomes that may be included in a personalized plan may be based on one or more reported aspects (e.g., intermediate outcomes that have been reported). By including one or more emulatable intermediate outcomes into a personalized plan, an end user may be able to better monitor his/her progress towards achieving the one or more target outcomes by comparing his/her actual intermediate results with the one or more emulatable intermediate outcomes that may be included in a personalized plan.

A "target outcome" may be any type of goal or desired result that may be sought by an end user or by a third party. Examples of target outcomes include, for example, health-related outcomes such as weight loss or improved cardiovascular conditioning, athletic outcomes such as developing a particular athletic skill including being able to pitch a curve ball or achieving a particular golf handicap, physiological outcomes such as reduced blood pressure or blood glucose levels, social outcomes such as obtaining membership into an elite social club or attaining a particular social status, mental state outcomes such as achieving certain level of calmness or happiness, interpersonal or relational outcomes such as having lots of friends or developing skill to make friends, employment outcomes such as being promoted or developing certain work skills, academic or intellectual outcomes, and so forth.

A source user may be any real or fictitious person who may be associated with one or more reported aspects. In some cases, a source user may be an actual (real) person who may be the source or is associated with one or more reported aspects. In other cases, a source user may be a fictional person such as a composite of multiple "actual" source users. For example, reported aspects indicating actual aspects of a plurality of real source users may be compiled and processed (e.g., normalized or averaged out) in order to create such a fictional source user.

Figure 1B:
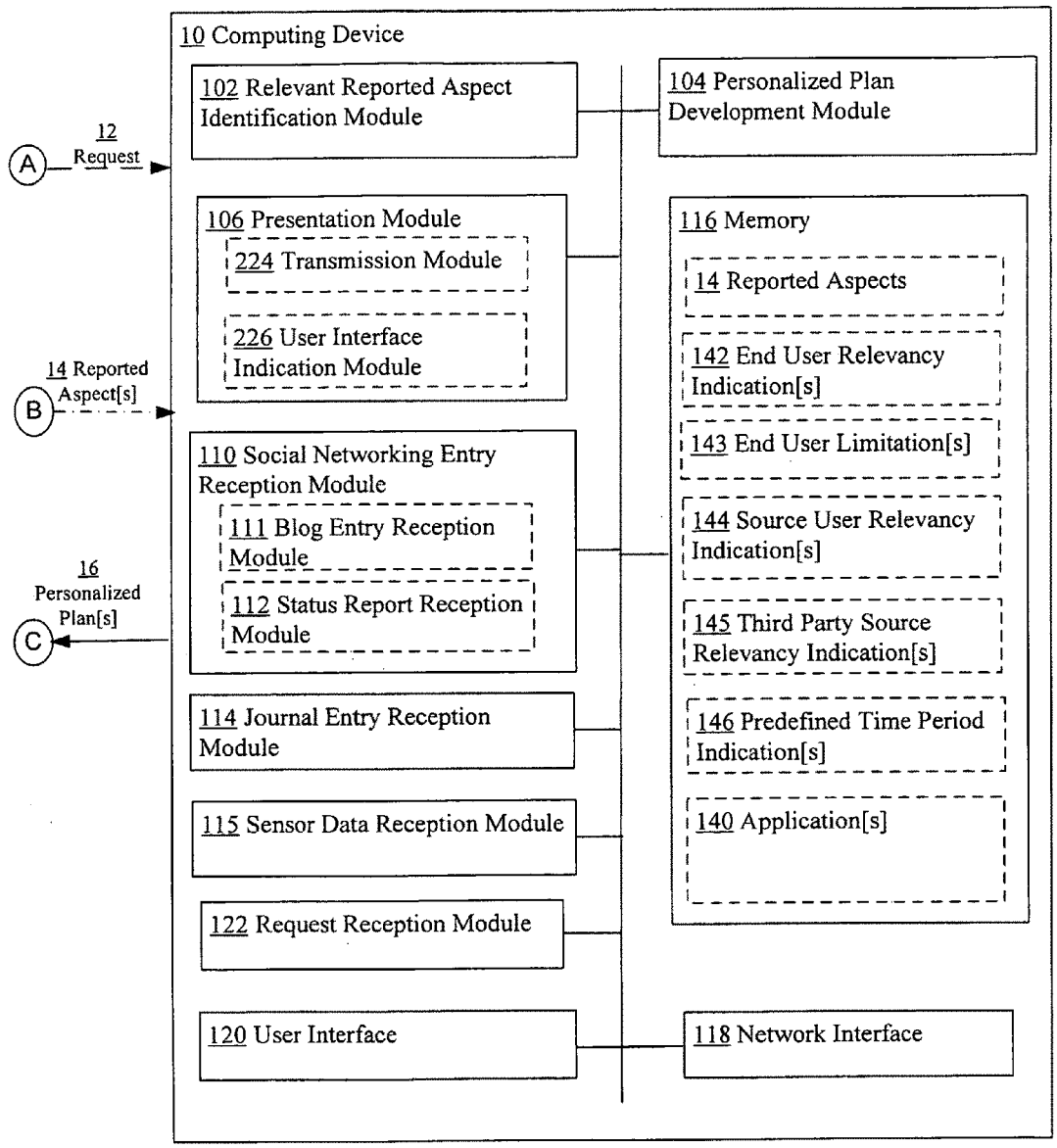

Turning now to FIGS. 1a, and 1b illustrating an example environment in which the methods, systems, circuitry, and computer program products in accordance with various embodiments may be implemented by a computing device 10. In various embodiments, the computing device 10 may be a server such as one of the one or more network servers 60, a source user device such as one of the local source user devices 20*, or an end user device such as the local end user device 30. More particularly, the methods, systems, circuitry, and computer program products may be implemented at any network device including a peer-to-peer network component device. In some embodiments, the computing device 10 may operate via a web 1.0 or web 2.0 construct. Note that in the following, "*" represents a wildcard. Thus, references in the following description to, for example, "a source user 2*" may be in reference to a source user 2a, a source user 2b, and so forth.

In various embodiments, the computing device 10 may be designed to, among other things, identify one or more relevant reported aspects associated with one or more source users 2* that are relevant to achieving one or more target outcomes, the identifying of the one or more relevant reported aspects being based, at least in part, on the one or more relevant reported aspects' relevancy with respect to the one or more target outcomes. After identifying the one or more relevant reported aspects, the computing device 10, may be designed to, among other things, develop one or more personalized plans 16 designed to facilitate an end user 4 to achieve the one or more target outcomes when one or more emulatable aspects indicated by the one or more personalized plans 16 are emulated, the development of the one or more personalized plans 16 being based, at least in part, on the identifying of the one or more relevant reported aspects.

In some implementations, the operation to identify the one or more relevant aspects may be prompted when the computing device 10, for example, receives a request 12 (e.g., a solicitation, a query, and so forth) from an end user 4 (e.g., via a local end user device 30), from a source user 2* (e.g., via a local source user device 20*), from a network server 60, or from a third party 6 (e.g., a network service provider, a content provider, and so forth). For these implementations, the request 12 may at least indicate one of the one or more target outcomes, and in some cases, may request for the one or more personalized plans 16. In some implementations, the request 12 may not indicate a source user 2*, and in particular, may not indicate any source user 2* who may have successfully achieved the one or more target outcomes.

As illustrated, in various embodiments the computing device 10 may be employed in a network environment. For example, the computing device 10 may communicate with other network devices (e.g., a local end user device 30, one or more network servers 60, one or more local source user devices 20*, one or more sensing devices 40, and so forth) via a wireless network and/or wired network 50 (e.g., at least one of a wireless network and a wired network 50). In various implementations, the wireless and/or wired network 50 may include at least one of a local area network (LAN), a wireless local area network (WLAN), personal area network (PAN), Worldwide Interoperability for Microwave Access (WiMAX), public switched telephone network (PTSN), general packet radio service (GPRS), cellular networks, and/or other types of wireless and/or wired networks 50.

Note again that in various alternative implementations the computing device 10 may be a server, a source user device (e.g., local source user device 20*), or an end user device (e.g., local end user device 30). However, for ease of explanation and understanding, the following description of the exemplary environment of FIGS. 1a and 1b will be from a perspective in which the computing device 10 is operating as a server rather than as an end user device or as a source user device. And although the computing device 10 in the following will be described from a server perspective (e.g., server embodiment), the following description of the functionalities of the computing device 10 will generally hold true even if the computing device 10 were operating as a source user device (e.g., source user embodiment) or as an end user device (e.g., end user embodiment) with a few minor exceptions.

For example, if the computing device 10 is a source user device such as a local source user device 20*, then the computing device 10 may directly communicate with a source user 2* via a user interface 120 rather through a wireless network and/or a wired network 50 as is the case when the computing device 10 is a server. Similarly, if the computing device 10 is an end user device such as a local end user device 30, then the computing device 10 may directly communicate with an end user 4 via the user interface 120 instead of through the wireless network and/or the wired network 50.

Referring particularly now to FIGS. 1a and 1b, which illustrates an example environment in accordance with various embodiments. Included in the illustrated environment of FIGS. 1a and 1b is an exemplary system 100, which includes at least a computing device 10 that may be designed to communicate with one or more source users 2* (via one or more local source user devices 20*) and an end user 4 (via a local end user device 30) through a wireless network and/or wired network 50. In some implementations, the computing device 10 may further communicate with, via the wireless network and/or wired network 50, one or more third parties 6 (e.g., one or more other end users 4, one or more content providers, one or more network service providers, and/or one or more other parties), one or more other network servers 60, and/or one or more sensing devices 40.

With respect to the one or more sensing devices 40, the one or more sensing devices 40 may communicate with the wireless network and/or the wired network 50 directly or indirectly via the one or more local source user devices 20*. As will be further described herein with respect to FIG. 2c, each of the one or more sensing devices 40 (see FIG. 2c) may include one or more sensors 240, a network interface 242, and/or a memory 244. The one or more sensors 240 may be designed to detect or sense one or more aspects associated with one or more source users 2*. Examples of sensors 240 include, for example, devices that can detect physical or physiological characteristics of one or more source users 2*, devices that can detect activities of the one or more source users 2*, devices that can detect external events (e.g., environmental conditions including the weather, pollution levels, performance of the stock market, and so forth), image capturing device such as a digital camera or camcorder, and/or devices that can detect the location of the one or more source users 2* such as a global positioning system or GPS. Examples of devices that can detect physical or physiological characteristics include, for example, a heart rate monitor, a blood pressure sensor, a glucose sensor, and so forth. Examples of devices that can detect activities of the one or more source users 2* including, for example, a pedometer, a toilet monitoring system (e.g., to monitor bowel movements), exercise machine sensors, an accelerometer to measure a person's movements which may indicate specific activities, and so forth.

In various implementations, the computing device 10 may be a computing/communication device that is designed to interface with a wireless network and/or wired network 50. In some embodiments, the computing device 10 may be a network server 60 that may be located at a single network site, located across multiple network sites, or a conglomeration of servers located at multiple network sites. In embodiments in which the computing device 10 is a source user device (e.g., local source user device 20*) or an end user device (e.g., local end user device 30*), the computing device 10 may be any one of a wide range of mobile or stationary computing/communication devices including, for example, a laptop, a desktop, a workstation, a cellular telephone, a personal digital assistant (PDA), a Smartphone, a web tablet such as a Netbook, and so forth.

The one or more source users 2* may comprise a first source user 2a, a second source user 2b, a third source user 2c, a fourth source user 2d, and so forth. The one or more local source user devices 20* may include a first local source user device 20a (e.g., to be used by the first source user 2a to communicate via wireless network and/or wired network 50), a second local source user device 20b (e.g., to be used by the second source user 2b to communicate via wireless network and/or wired network 50), and so forth. The one or more local source user devices 20* and the local end user device 30 (as well as the computing device 10 in embodiments in which the computing device 10 is an end user device or a source user device) may be any one of a variety of computing/communication devices including, for example, a cellular phone, a personal digital assistant (PDA), a laptop, a desktop, or other types of computing/communication devices.

In some embodiments, the one or more local source user devices 20 and/or the local end user device 30 (as well as the computing device 10 in some embodiments) may be a handheld device such as a cellular telephone, a Smartphone, a Mobile Internet Device (MID), an Ultra Mobile Personal Computer (UMPC), a convergent device such as a personal digital assistant (PDA), and so forth. Alternatively, such local client devices (e.g., local source user device 20 and/or local end user device 30) may be a laptop, a desktop, a workstation, a web tablet such as a Netbook, or other types of devices that may not be a handheld device in various alternative implementations.

Referring back to the exemplary environment of FIGS. 1a and 1b, the computing device 10 in various implementations may be designed to collect one or more reported aspects 14 (e.g., in the form of data) from one or more sources including, for example, one or more local source user devices 20*, one or more sensing devices 40, one or more network servers 60, and/or one or more third parties 6. In some implementations, the one or more reported aspects 14 to be collected may indicate one or more aspects associated with one or more source users 2*. The reported aspects 14 may be received in a variety of forms including, for example, log entries such as blog entries, status reports, journal entries, entries provided by sensing devices 40, and/or other types of entries. In embodiments where the computing device 10 is a source user device (e.g., local source user device 20*), the computing device 10 may receive reported aspects 14 through a user interface 120. In some cases, after collecting the reported aspects 14, the reported aspects 14 may be stored in a memory 116.

In some implementations, the computing device 10 may be designed to receive a request 12 (e.g., a solicitation for one or more personalized plans 16) from a variety of different sources. For example, the request 12 may be received from an end user 4, from a third party 6, from a source user 2*, or from a network server 60. For these embodiments, the request 12 may at least identify one or more target outcomes of one or more personalized plans 16, and in some cases, may not identify any source users 2* who may have achieved the one or more target outcomes. In embodiments where the computing device 10 is a source user device or an end user device, the computing device 10 may receive the request 12 via a user interface 120.

In response to receiving the request 12, the computing device 10 may identify one or more relevant reported aspects associated with the one or more source users 2* that are relevant to achieving one or more target outcomes, the identifying of the one or more relevant reported aspects being based, at least in part, on the one or more relevant reported aspects' relevancy with respect to the one or more target outcomes. The identification of the one or more relevant reported aspects may be based on one or more factors including relevancy factors as will be further described herein. Further, the identification of the one or more relevant reported aspects may be from a plurality of reported aspects that include both reported aspects that may be relevant for achieving the one or more target outcomes and reported aspects that may not be relevant for achieving the one or more target outcomes. In any event, based on the identification of the one or more relevant reported aspects, the computing device 10 may be designed to develop one or more personalized plans 16 designed to facilitate an end user 4 to achieve the one or more target outcomes when one or more emulatable aspects included in the one or more personalized plans 16 are emulated.

Figure 2A:
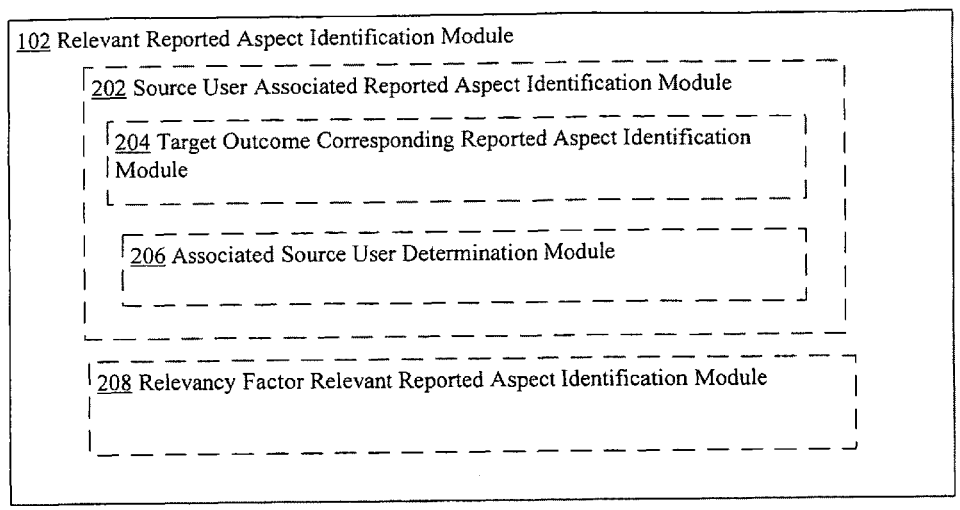
FIG. 2a shows another perspective of the Relevant Reported Aspect Identification Module 102 of the Computing Device 10 of FIG. 1b.

The computing device 10 as illustrated in FIG. 1b may include a variety of modules, sub-modules, and various other components. As shown, the computing device 10 may include a relevant reported aspect identification module 102 (which may further include one or more sub-modules as illustrated in FIG. 2a), a personalized plan development module 104 (which may further include one or more sub-modules as illustrated in FIG. 2b), a presentation module 106 (which may further include a transmission module 224 and/or a user interface indication module 226), a memory 116 (which may store a plurality of reported aspects 14, one or more end user relevancy indications 142, one or more end user limitations 143, one or more source user relevancy indications 144, one or more third party source relevancy indications 145, one or more predefined time period indications 146, and/or one or more applications 140), a network interface 118 (e.g., network interface card or NIC), and/or a user interface 120. In various embodiments, the computing device 10 may further include a social networking entry reception module 110 (which may further include a blog entry reception module 111 and/or a status report reception module 112), a journal entry reception module 114, and/or a sensor data reception module 115. In various implementations, the computing device 10 may include a request reception module 122 designed to receive one or more requests 12 via, for example, a wireless network and/or wired network 50. For these implementations, the one or more requests 12 to be received may be for one or more personalized plans 16.

The relevant reported aspect identification module 102 may be configured to, among other things, identify one or more relevant reported aspects based, at least in part, on the one or more relevant reported aspects' relevancy with respect to one or more target outcomes, the one or more relevant reported aspects to be identified being associated with one or more source users 2* and being relevant to achieving the one or more target outcomes. The personalized plan development module 104 may be configured to, among other things, develop one or more personalized plans 16 based, at least in part, on the one or more relevant reported aspects, the one or more personalized plans 16 to be developed being designed to facilitate an end user 4 to achieve the one or more target outcomes when one or more emulatable aspects indicated by the one or more personalized plans 16 are emulated. The presentation module 106 may be designed to present (e.g., transmit via the wireless network and/or wired network 50 to the local end user device 30, to one or more local source user devices 20, to one or more network servers 60, and/or to one or more third parties 6) the one or more personalized plans 16 that are developed. A more detailed discussion relating to the relevant reported aspect identification module 102, the personalized plan development module 104, the presentation module 106, and their sub-modules, will be provided below with respect to the various operational flows to be described herein.

The memory 116 may be designed to store various data including a plurality of reported aspects 14 that may include one or more reported aspects associated with one or more source users 2* and that may or may not be relevant to achieving the one or more target outcomes (e.g., the plurality of reported aspects 14 may include both reported aspects that are relevant to achieving one or more target outcomes and reported aspects that may not be relevant to achieving the one or more target outcomes). Other types of data may be stored in the memory 116 including, for example, one or more end user relevancy indications 142 (e.g., one or more indications that indicate the types of reported or emulatable aspects that an end user 4 has an interest in or believes is relevant to achieving one or more target outcomes), one or more end user limitations 143 (e.g., limitations such as contextual limitations, physical limitations, personal limitations, and so forth, associated with the end user 4 that prevent one or more emulatable aspects from being emulated), and/or one or more source user relevancy indications 144 (e.g., one or more indications provided by a source user 2* that indicate at least which types of reported aspects are relevant to achieving one or more target outcomes).

In some cases, the memory 116 may also include, for example, one or more third party source relevancy indications 145 (e.g., one or more indications provided by one or more third party sources such as one or more third parties 6 that indicate at least which types of reported aspects are relevant to achieving one or more target outcomes), one or more predefined time period indications 146 (e.g., one or more indications that indicate at least one time period such as a time increment or window that may be used to determine whether, for example, a reported aspect is relevant for achieving at least one target outcome only if the reported aspect indicate an aspect that occurred within the at least one time period from an occurrence of the target outcome as successfully achieved by, for example, a source user 2*), and/or one or more applications 140 (e.g., a text messaging application, an instant messaging application, an email application, a voice recognition system, a Web 1.0 application, and/or Web 2.0 application to facilitate in communicating via, for example, the World Wide Web). In various implementations, the memory 116 comprises one or more of a mass storage device, a read-only memory (ROM), a programmable read-only memory (PROM), an erasable programmable read-only memory (EPROM), a cache memory such as random access memory (RAM), a flash memory, a synchronous random access memory (SRAM), a dynamic random access memory (DRAM), and/or other types of memory devices.

The social networking entry reception module 110 may be configured to receive social networking entries from one or more sources including, for example, from one or more source users 2*, an end user 4, one or more third parties 6, and/or one or more network servers 60. The social networking entry reception module 110 may further include a blog entry reception module 111 for receiving blog entries (e.g. microblog entries) and/or a status report reception module 112 for receiving social networking status reports. The journal entry reception module 114 may be configured to receive journal entries from, for example, the one or more source users 2, the end user 4, and/or from the one or more third parties 6 (e.g., a non-user). The sensor data reception module 115 may be configured to receive sensing data from one or more sensing devices 40. The user interface 120 may include one or more of, for example, a display monitor, a touchscreen, a keyboard, a keypad, a mouse, an audio system including one or more speakers, a microphone, an image capturing device such as a digital camera, and so forth.

FIG. 2a illustrates particular implementations of the relevant reported aspect identification module 102 of the computing device 10 of FIG. 1b. As illustrated, the relevant reported aspect identification module 102 may include, in various implementations, one or more sub-modules. For example, in some implementations, the relevant reported aspect identification module 102 may include a source user associated reported aspect identification module 202 that is configured to, among other things, identify from a plurality of reported aspects 14 one or more reported aspects 14 that are associated with one or more source users 2*, the one or more source users 2* having achieved one or more target outcomes. The identification of one or more relevant reported aspects that are relevant to achieving the one or more target outcomes by the relevant reported aspect identification module 102 may be facilitated by at least identifying those reported aspects 14 that are associated with source users 2* who have been determined to have achieved the one or more target outcomes.

In order to facilitate the source user associated reported aspect identification module 202 identify the one or more reported aspects 14 that are associated with the one or more source users 2* who have achieved the one or more target outcomes, the source user associated reported aspect identification module 202 may further include a target outcome corresponding reported aspect identification module 204 and/or an associated source user determination module 206. The target outcome corresponding reported aspect identification module 204 may be configured to identify from the plurality of reported aspects 14 one or more reported aspects 14 that corresponds to the one or more target outcomes. In contrast, the associated source user determination module 206 may be configured to determine one or more source users 2* who are associated with the one or more reported aspects 14 that correspond to the one or more target outcomes (e.g., determine the one or more source users 2* who have achieved the one or more target outcomes).

In various implementations, the relevant reported aspect identification module 102 may further include a relevancy factor relevant reported aspect identification module 208 that is configured to at least identify one or more reported aspects 14 that are relevant with respect to one or more relevancy factors. Various types of relevancy factors may be considered as previously described including, for example, whether the one or more reported aspects 14 belong to the types of aspects that is of interest to the end user 4* or are considered as relevant to achieving the one or more target outcomes by a source user 2* or by a third party source.

FIG. 2b illustrates particular implementations of the personalized plan development module 104 of FIG. 1b. As previously indicated, the personalized plan development module 104 may be configured to develop one or more personalized plans 16 that are designed to facilitate an end user 4 to achieve one or more target outcomes when one or more emulated aspects included in the one or more personalized plans 16 are emulated, the development of the one or more personalized plans 16 being based on one or more relevant reported aspects that are identified by the relevant reported aspect identification module 102.

In various implementations, the personalized plan development module 104 may include one or more of an emulatable aspect inclusion module 220, a relationship defining module 222, an emulatable intermediate outcome inclusion module 223, a limitation compliance determination module 224 (which may include an action module 225 that may further include a non-compliance notification module 226 and/or a personalized plan modification module 228), and/or a plausible determination module 230 (which may include an action module 232 that may further include a not plausible notification module 234 and/or personalized plan modification module 236).

The emulatable aspect inclusion module 220 may be configured to include into each of the one or more personalized plans 16 to be developed one or more emulatable aspects that correspond to the one or more relevant reported aspects identified by the relevant reported aspect identification module 102. The relationship defining module 222 may be configured to define in each of the one or more personalized plans 16 to be developed one or more relationships (e.g., spatial, temporal, and/or specific time relationships) between a plurality of emulatable aspects that may be included in each of the one or more personalized plans 16. The emulatable intermediate outcome inclusion module 223 may be configured to include into at least one of the one or more personalized plans 16 to be developed one or more emulatable intermediate outcomes related to the one or more target outcomes of the at least one of the one or more personalized plans 16.

The limitation compliance determination module 224 may be configured to determine whether the one or more emulatable aspects to be included in the one or more personalized plans 16 complies with one or more limitations associated with the end user 4, and if not compliant, execute one or more actions (e.g., as executed by the action module 225). Various types of actions may be executed by the action module 225 if a determination is made of non-compliance. For example, in some implementations, the action module 225 may include a non-compliance notification module 226 that is configured to notify (e.g., notifying by transmitting a notification or by indicating via a user interface 120) at least one of the end user 4 and a third party 6 regarding non-compliance of the one or more emulatable aspects in response to a determination of non-compliance with the one or more limitations associated with the end user 4. Other types of actions by the action module 225 may also be executed in various implementations. For example, in some implementations, the action module 225 may include a personalized plan modification module 228 that is configured to modify the one or more personalized plans 16 including replacing one or more emulatable aspects that have been determined not to be in compliance with the one or more limitations associated with the end user 4 with one or more replacement emulatable aspects that does comply with the one or more limitations associated with the end user 4.

The plausible determination module 230, in contrast to the limitation compliance determination module 224, may be configured to determine whether at least one of the one or more emulatable aspects to be included in the one or more personalized plans 16 is a plausible aspect that has been successfully emulated by one or more third parties 6 (e.g., other end users 4), and if not plausible, execute one or more actions (e.g., as executed by the action module 232). Various types of actions may be executed by the action module 232 if a determination is made of non-compliance.

For example, in some implementations, the action module 232 may include a not plausible notification module 234 that is configured to notify, in response to determining that the at least one of the one or more emulatable aspects to be included in the one or more personalized plans 16 is not a plausible aspect, at least one of the end user 4 and a third party 6 regarding the determination that the at least one of the one or more emulatable aspects to be included in the one or more personalized plans 16 is not a plausible aspect. Note that in some implementations, a "plausible aspect" may be an aspect that has been successfully emulated by one or more third parties 6 in order to, for example, achieve the one or more target outcomes.

Other types of actions may also be executed by the action module 232 when one or more emulatable aspects that may be included in the one or more personalized plans 16 have been determined to be not plausible. For example, in some implementations, the action module 232 may include a personalized plan modification module 236 that is configured to modify, in response to a determination that at least one of the one or more emulatable aspects included in the one or more personalized plans 16 is not a plausible aspect, at least one of the one or more personalized plans 16 by replacing the at least one of the one or more emulatable aspects determined to be not a plausible aspect with at least one replacement emulatable aspect that is a plausible aspect that has been successfully emulated by one or more third parties 6.

Figure 2C:
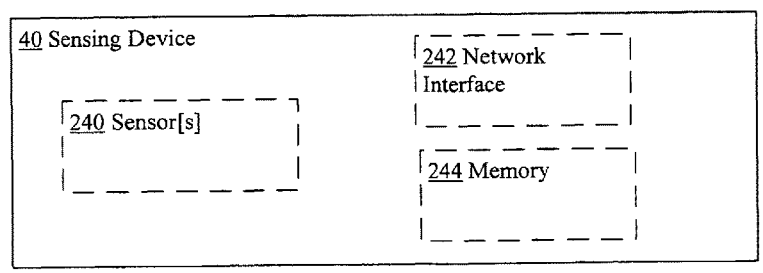
FIG. 2c shows one perspective of one of the Sensing Devices 40 of the environment of FIGS. 1a and 1b.
Figure 2B:
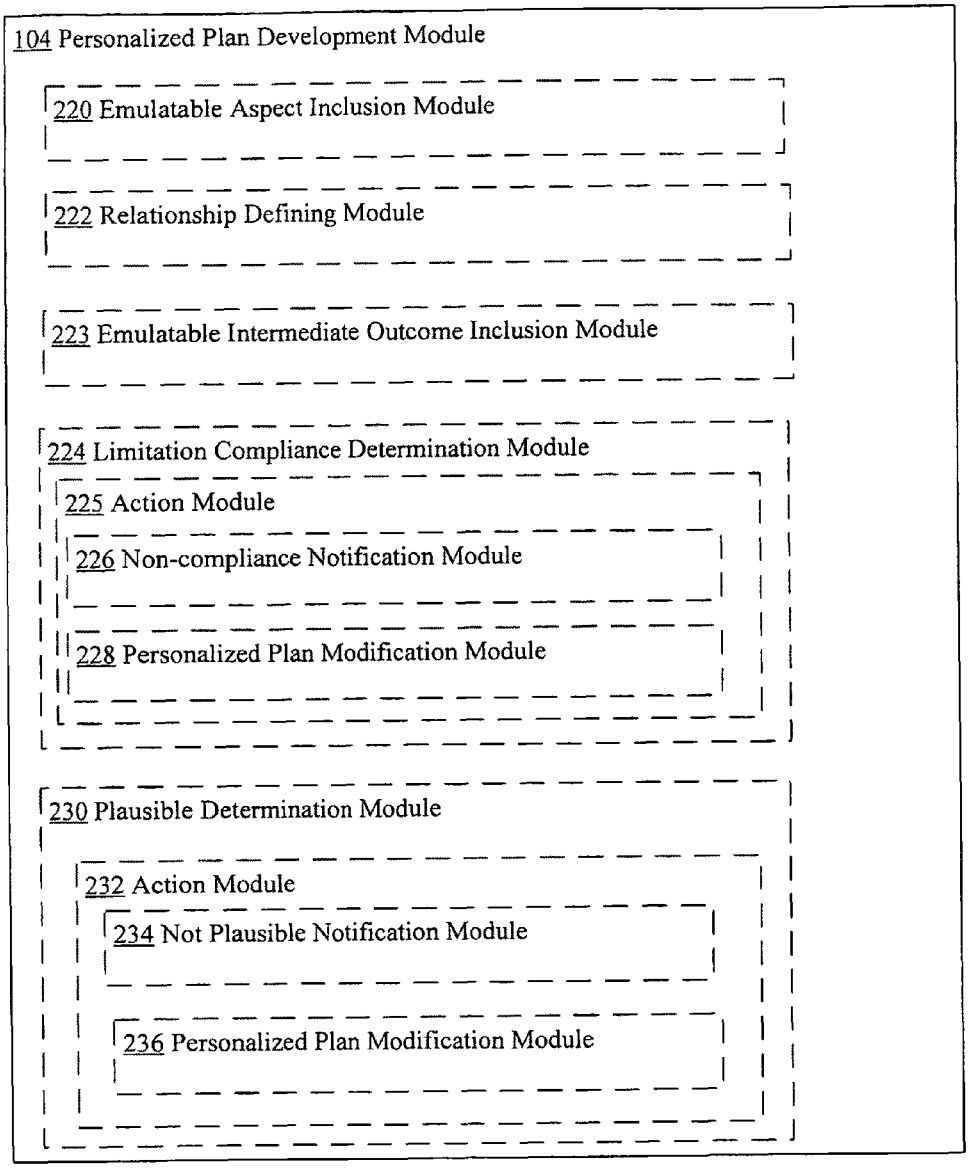
FIG. 2b shows another perspective of the Personalized Plan Development Module 104 of the Computing Device 10 of FIG. 1b.

Referring now to FIG. 2c illustrating one of the sensing devices 40 of FIGS. 1a and 1b. The sensing device 40, in various embodiments, may include at least one or more sensors 240. The one or more sensors 240 that may be included in a sensing device 40 may be designed to sense or detect one or more aspects associated with a source user 2*. For example, in various implementations, the one or more sensors 240 may include one or more devices that can monitor a user's physiological characteristics such as blood pressure sensors, heart rate monitors, glucometers (e.g., glucose meters), and so forth.

In some implementations, the one or more sensors 240 may include devices that can detect activities of a user (e.g., a source user 2*). Examples of such devices include, for example, a pedometer, a toilet monitoring system (e.g., to monitor bowel movements), exercise machine sensors, an accelerometer to measure a person's movements which may indicate specific activities, and so forth. The one or more sensors 240 may include, in various implementations, other types of sensor/monitoring devices such as video or digital camera to provide electronic images of, for example, the one or more target outcomes as displayed by a source user 2*, global positioning system (GPS) to provide location data related to a user (e.g., locations of the source user 2*), and so forth. In various implementations, a sensing device 40 may further include a network interface 242 and/or a memory 244 to store, for example, sensing data provided by the one or more sensors 240.

Referring back to the computing device 10 of FIG. 1b, the various modules (e.g., the relevant reported aspect identification module 102, the personalized plan development module 104, the presentation module 106, and so forth) along with their sub-modules included in the computing device 10 may be implemented using hardware, software, firmware, or any combination thereof. For example, in some implementations, the relevant reported aspect identification module 102, the personalized plan development module 104, and/or the presentations module 106 may be implemented with a processor 802 (e.g., microprocessor, controller, and so forth) executing computer readable instructions 804 (e.g., computer program product) stored in a storage medium 806 (e.g., volatile or non-volatile memory) such as a signal-bearing medium as depicted in the computing device 800 of FIG. 8. Alternatively, hardware such as application specific integrated circuit (ASIC) may be employed in order to implement such modules in some alternative implementations.

Figure 3:
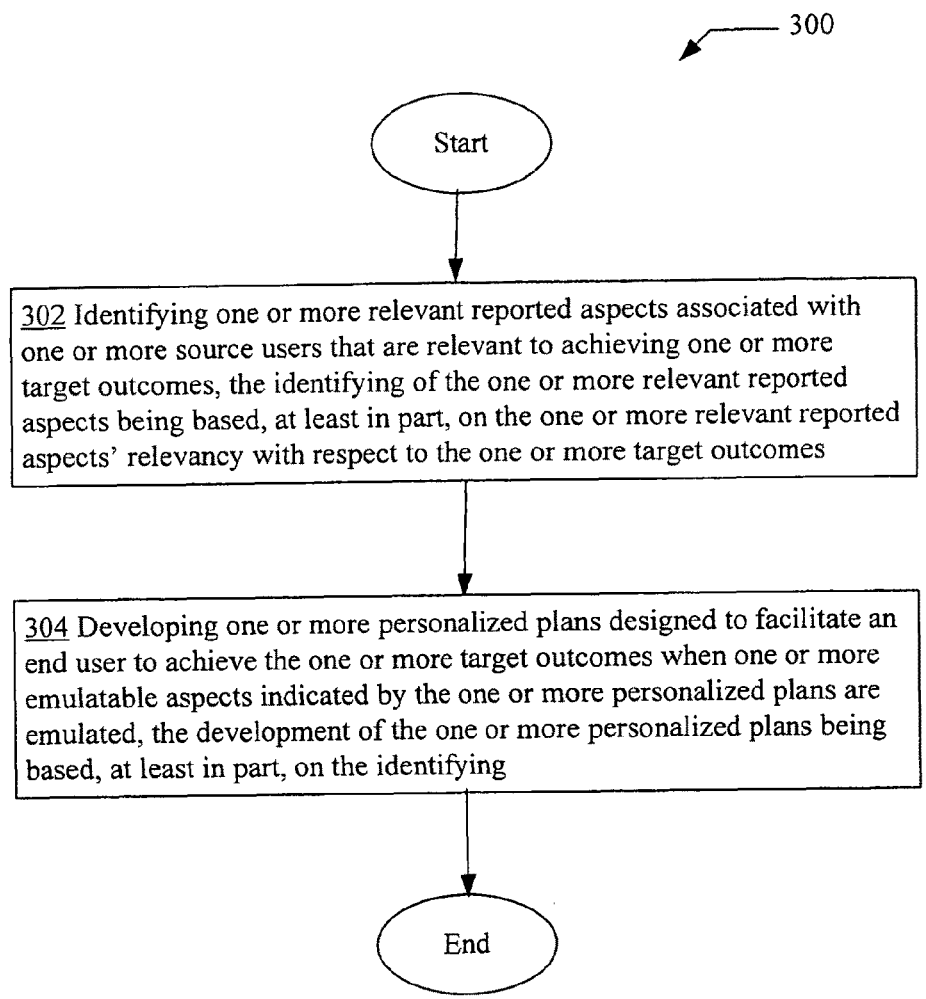
FIG. 3 is a high-level logic flowchart of a process.

A more detailed discussion related to the computing device 10 of FIG. 1*b* will now be provided with respect to the processes and operations to be described herein. FIG. 3 illustrates an operational flow 300 representing example operations related to, among other things, identification of one or more relevant reported aspects associated with one or more source users 2* that are relevant to achieving one or more target outcomes, the identification being based on the relevancy of the one or more relevant reported aspects with respect to the one or more target outcomes, and the development of one or more personalized plans 16 based on the one or more relevant reported aspects that are identified.

In FIG. 3 and in the following figures that include various examples of operational flows, discussions and explanations may be provided with respect to the exemplary environments described above as illustrated in FIGS. 1*a* and 1*b*, and/or with respect to other examples (e.g., as provided in FIGS. 2*a*, 2*b*, and 2*c*) and contexts. However, it should be understood that the operational flows may be executed in a number of other environments and contexts, and/or in modified versions of FIGS. 1*a*, 1*b*, 2*a*, 2*b*, and 2*c*. Also, although the various operational flows are presented in the sequence(s) illustrated, it should be understood that the various operations may be performed in other orders than those which are illustrated, or may be performed concurrently.

Further, in FIG. 3 and in the figures to follow thereafter, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to a relevant reported aspect identifying operation 302 for identifying one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes. For instance, and as an illustration, the relevant reported aspect identification module 102 of the computing device 10 of FIG. 1*b* identifying (e.g., determining, ascertaining, finding, locating, and so forth) one or more relevant reported aspects associated with one or more source users 2 and that are relevant to achieving one or more target outcomes, the identifying of the one or more relevant reported aspects being based, at least in part, on the one or more relevant reported aspects' relevancy with respect to the one or more target outcomes.

Note that in various implementations, the identification of the one or more relevant reported aspects may not depend on the identification (e.g., by an end user 4 or by a third party 6), at least initially, of the one or more source users 2* who have achieved the one or more target outcomes. Rather, such identification operation may depend, at least initially, only on the relevancy of the one or more relevant reported aspects with respect to the one or more target outcomes in order to identify the one or more relevant reported aspects.

In addition to the relevant reported aspect identifying operation 302, operational flow 300 may also include a personalized plan developing operation 304 for developing one or more personalized plans designed to facilitate an end user to achieve the one or more target outcomes when one or more emulatable aspects indicated by the one or more personalized plans are emulated, the development of the one or more personalized plans being based, at least in part, on the identifying. For instance, the personalized plan development module 104 of the computing device 10 developing (e.g., creating) one or more personalized plans 16 designed to facilitate an end user 4 to achieve the one or more target outcomes when one or more emulatable aspects indicated by the one or more personalized plans 16 are emulated, the development of the one or more personalized plans 16 being based, at least in part, on the identifying of the one or more relevant reported aspects. As will be described herein, the relevant reported aspect identifying operation 302 as well as the personalized plan developing operation 304 may be implemented in a number of different ways in various alternative implementations.

Figure 4A:
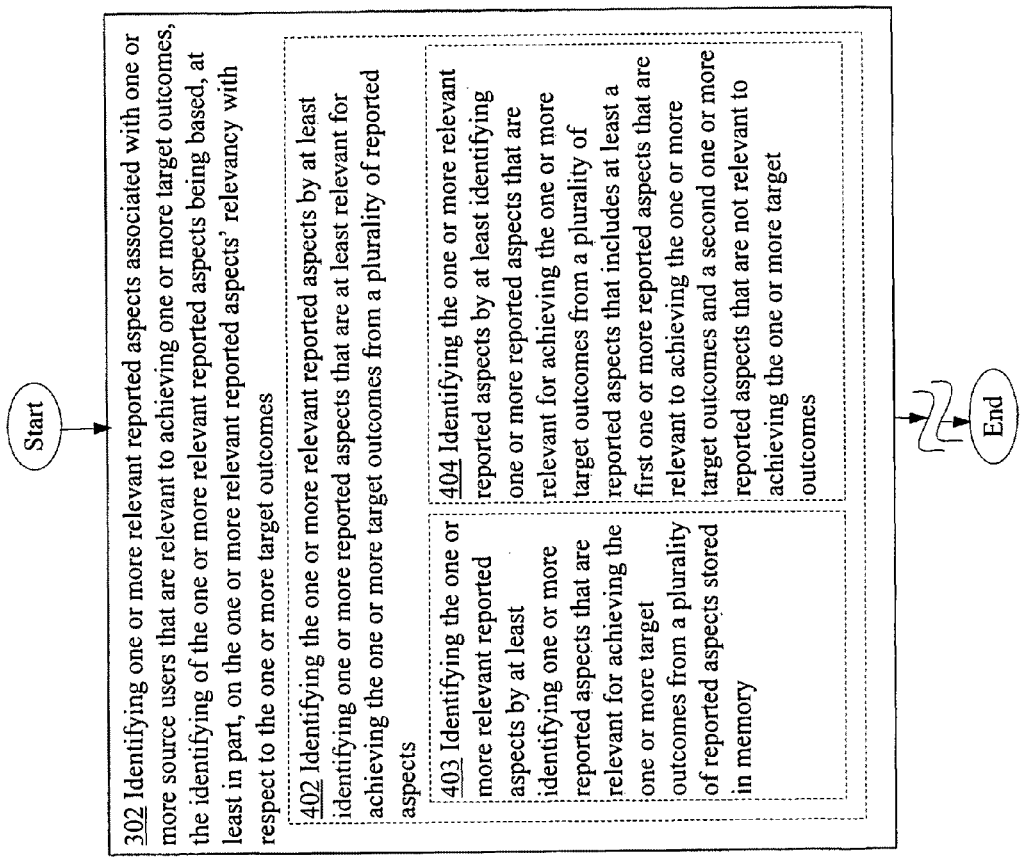
FIG. 4a is a high-level logic flowchart of a process depicting alternate implementations of the relevant reported aspect identifying operation 302 of FIG. 3.

For example the relevant reported aspect identifying operation 302 of FIG. 3 in various implementations may be executed in various alternative ways as will be illustrated in FIGS. 4*a*, 4*b*, 4*c*, 4*d*, 4*e*, 4*f*, 4*g*, and 4*h*. In some implementations, for example, the relevant reported aspect identifying operation 302 may include an operation 402 for identifying the one or more relevant reported aspects by at least identifying one or more reported aspects that are at least relevant for achieving the one or more target outcomes from a plurality of reported aspects as depicted in FIG. 4*a*. For instance, the relevant reported aspect identification module 102 of the computing device 10 of FIG. 1*b* identifying the one or more relevant reported aspects by at least identifying one or more reported aspects 14 (e.g., aspects of the one or more source users 2* that have been reported and that may indicate, for example, the behaviors or acts of the one or more source users 2*) that are at least relevant for achieving the one or more target outcomes from a plurality of reported aspects 14.

In some implementations, operation 402 may further include an operation 403 for identifying the one or more relevant reported aspects by at least identifying one or more reported aspects that are relevant for achieving the one or more target outcomes from a plurality of reported aspects stored in memory as depicted in FIG. 4*a*. For instance, the relevant reported aspect identification module 102 of the computing device 10 identifying the one or more relevant reported aspects by at least identifying one or more reported aspects 14 that are relevant for achieving the target outcomes from a plurality of reported aspects 14 stored in memory 116 (e.g., volatile memory, non-volatile memory, cache memory, and so forth).

In the same or different implementations, operation 402 may include an operation 404 for identifying the one or more relevant reported aspects by at least identifying one or more reported aspects that are relevant for achieving the one or more target outcomes from a plurality of reported aspects that includes at least a first one or more reported aspects that are relevant to achieving the one or more target outcomes and a second one or more reported aspects that are not relevant to achieving the one or more target outcomes as further depicted in FIG. 4*a*. For instance, the relevant reported aspect identification module 102 of the computing device 10 identifying the one or more relevant reported aspects by at least identifying one or more reported aspects 14 that are relevant for achieving the one or more target outcomes from a plurality of reported aspects 14 that includes at least a first one or more reported aspects 14 that are relevant to achieving the one or more target outcomes and a second one or more reported aspects 14 that are not relevant to achieving the one or more target outcomes.

Figure 4B:
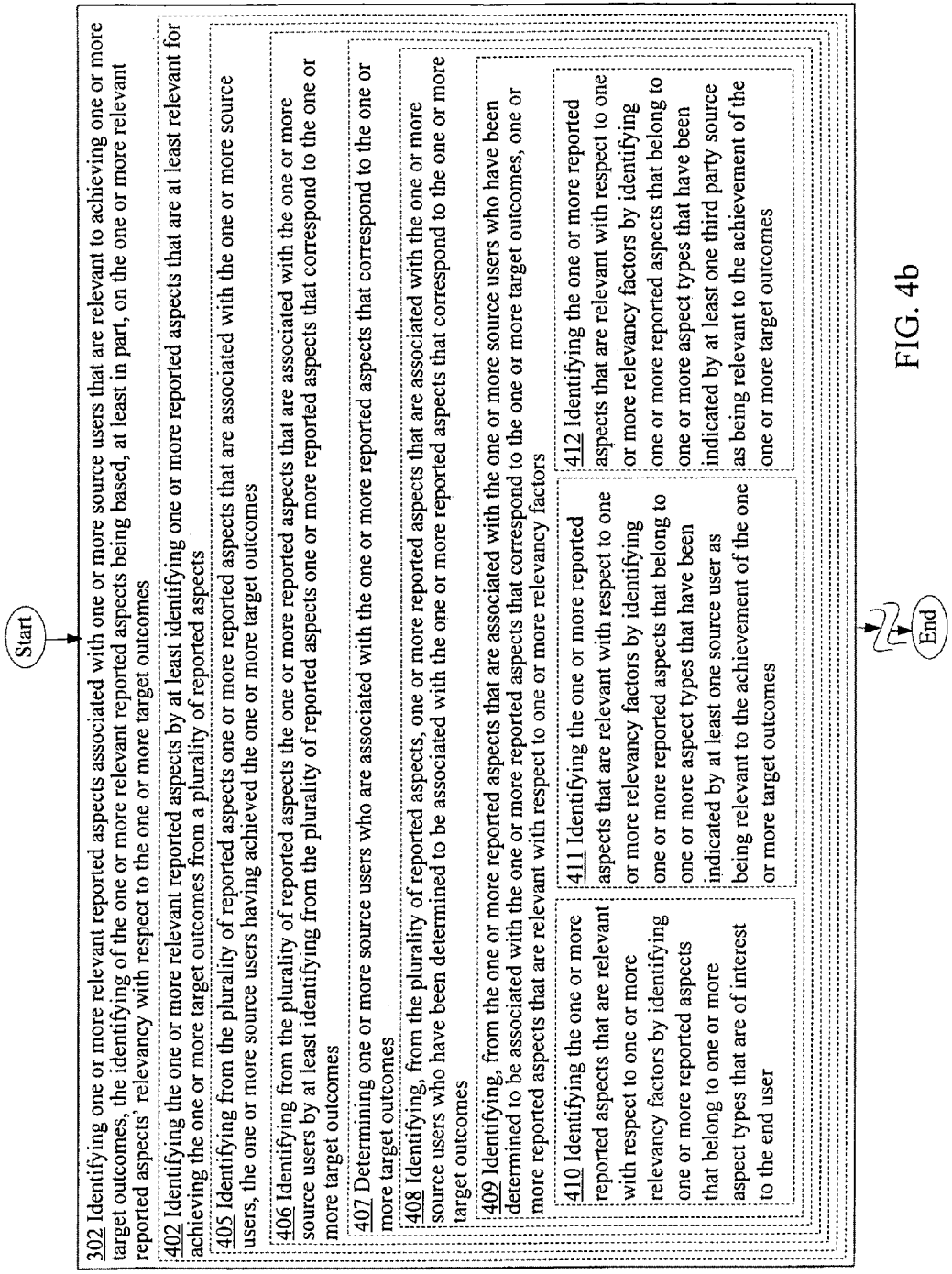
FIG. 4b is a high-level logic flowchart of a process depicting alternate implementations of the relevant reported aspect identifying operation 302 of FIG. 3.

Various techniques may be employed in order to identify reported aspects 14 that may be relevant for achieving a particular target outcome or outcomes. In some cases, this may involve at least identifying reported aspects 14 that are associated with one or more source users 2* who have been determined to have achieved the target outcome or outcomes. For example, in some implementations, operation 402 may include an operation 405 for identifying from the plurality of reported aspects one or more reported aspects that are associated with the one or more source users, the one or more source users having achieved the one or more target outcomes as depicted in FIG. 4b. For instance, the source user associated reported aspect identification module 202 (see FIG. 2a) of the computing device 10 identifying from the plurality of reported aspects 14 one or more reported aspects that are associated with the one or more source users 2*, the one or more source users 2* having achieved the one or more target outcomes.

In order to determine whether the one or more source users 2* have achieved the one or more target outcomes, operation 405 may further include one or more additional operations. For example, in some implementations, operation 405 may include an operation 406 for identifying from the plurality of reported aspects the one or more reported aspects that are associated with the one or more source users by at least identifying from the plurality of reported aspects one or more reported aspects that correspond to the one or more target outcomes as depicted in FIG. 4b. For instance, the target outcome corresponding reported aspect identification module 204 (see FIG. 2a) of the computing device 10 identifying from the plurality of reported aspects 14 the one or more reported aspects 14 that are associated with the one or more source users 2* by at least identifying from the plurality of reported aspects 14 one or more reported aspects 14 that corresponds (e.g., equivalent or substantially equivalent) to the one or more target outcomes.

Operation 406, in turn, may further include an operation 407 for determining one or more source users who are associated with the one or more reported aspects that correspond to the one or more target outcomes as depicted in FIG. 4b. For instance, the associated source user determination module 206 (see FIG. 2a) of the computing device 10 determining one or more source users 2* (e.g., Matthew and Leslie) who are associated with the one or more reported aspects 14 (e.g., Matthew and Leslie getting a 92 percent and 95 percent test scores, respectively, on a particular calculus test) that correspond to the one or more target outcomes (e.g., achieving at least a 90 percent test score on the calculus test).

For these implementations, once the one or more source users 2* who have achieved the one or more target outcomes have been identified, reported aspects that are associated with the source users 2** may be identified. For example, in some implementations, operation 407 may further include an operation 408 for identifying, from the plurality of reported aspects, one or more reported aspects that are associated with the one or more source users who have been determined to be associated with the one or more reported aspects that correspond to the one or more target outcomes as depicted in FIG. 4b. For instance, the source user associated reported aspect identification module 202 of the computing device 10 identifying, from the plurality of reported aspects 14, one or more reported aspects 14 that are associated with the one or more source users 2* who have been determined to be associated with the one or more reported aspects 14 that correspond to the one or more target outcomes. In other words, the source user associated reported aspect identification module 202 identifying one or more reported aspects 14 that are associated with source users 2* who have been determined to have achieved the one or more target outcomes.

Note that not all reported aspects 14 that are associated with the source users 2* who have been determined to have achieved the one or more target outcomes may actually be relevant to achieving the one or more target outcomes. Thus, operation 408 may further include one or more additional operations in order to identify reported aspects 14 that are relevant to achieving the one or more target outcomes. For example, in some implementations, operation 408 may further include an operation 409 for identifying, from the one or more reported aspects that are associated with the one or more source users who have been determined to be associated with the one or more reported aspects that correspond to the one or more target outcomes, one or more reported aspects that are relevant with respect to one or more relevancy factors as depicted in FIG. 4b. For instance, the relevancy factor relevant reported aspect identification module 208 (see FIG. 2a) of the computing device 10 identifying, from the one or more reported aspects 14 that are associated with the one or more source users 2* who have been determined to be associated with the one or more reported aspects that correspond to the one or more target outcomes, one or more reported aspects 14 that are relevant with respect to one or more relevancy factors.

Various types of relevancy factors may be considered when determining whether a reported aspect is relevant to the achievement of a particular target outcome or outcomes. For example, in some implementations, operation 409 may include an operation 410 for identifying the one or more reported aspects that are relevant with respect to one or more relevancy factors by identifying one or more reported aspects that belong to one or more aspect types that are of interest to the end user as depicted in FIG. 4b. For instance, the relevancy factor relevant reported aspect identification module 208 of the computing device 10 identifying the one or more reported aspects 14 that are relevant with respect to one or more relevancy factors by identifying one or more reported aspects 14 that belong to one or more aspect types (e.g., sleep or rest activities) that are of interest to the end user 4.

In the same or different implementations, operation 409 may include an operation 411 for identifying the one or more reported aspects that are relevant with respect to one or more relevancy factors by identifying one or more reported aspects that belong to one or more aspect types that have been indicated by at least one source user as being relevant to the achievement of the one or more target outcomes as depicted in FIG. 4b. For instance, the relevancy factor relevant reported aspect identification module 208 of the computing device 10 identifying the one or more reported aspects that are relevant with respect to one or more relevancy factors by identifying one or more reported aspects that belong to one or more aspect types (e.g., reading activities) that have been indicated by at least one source user 2* as being relevant to the achievement of the one or more target outcomes (e.g., improve verbal test score on the scholastic amplitude test).

In the same or different implementations, operation 409 may include an operation 412 for identifying the one or more reported aspects that are relevant with respect to one or more relevancy factors by identifying one or more reported aspects that belong to one or more aspect types that have been indicated by at least one third party source as being relevant to the achievement of the one or more target outcomes as depicted in FIG. 4b. For instance, the relevancy factor relevant reported aspect identification module 208 of the computing device 10 identifying the one or more reported aspects 14 that are relevant with respect to one or more relevancy factors by identifying one or more reported aspects 14 that belong to one or more aspect types (e.g., exercise activities or dietary activities) that have been indicated by at least one third party source (e.g., published medical research) as being relevant to the achievement of the one or more target outcomes (e.g., mental well-being).

Figure 4C:
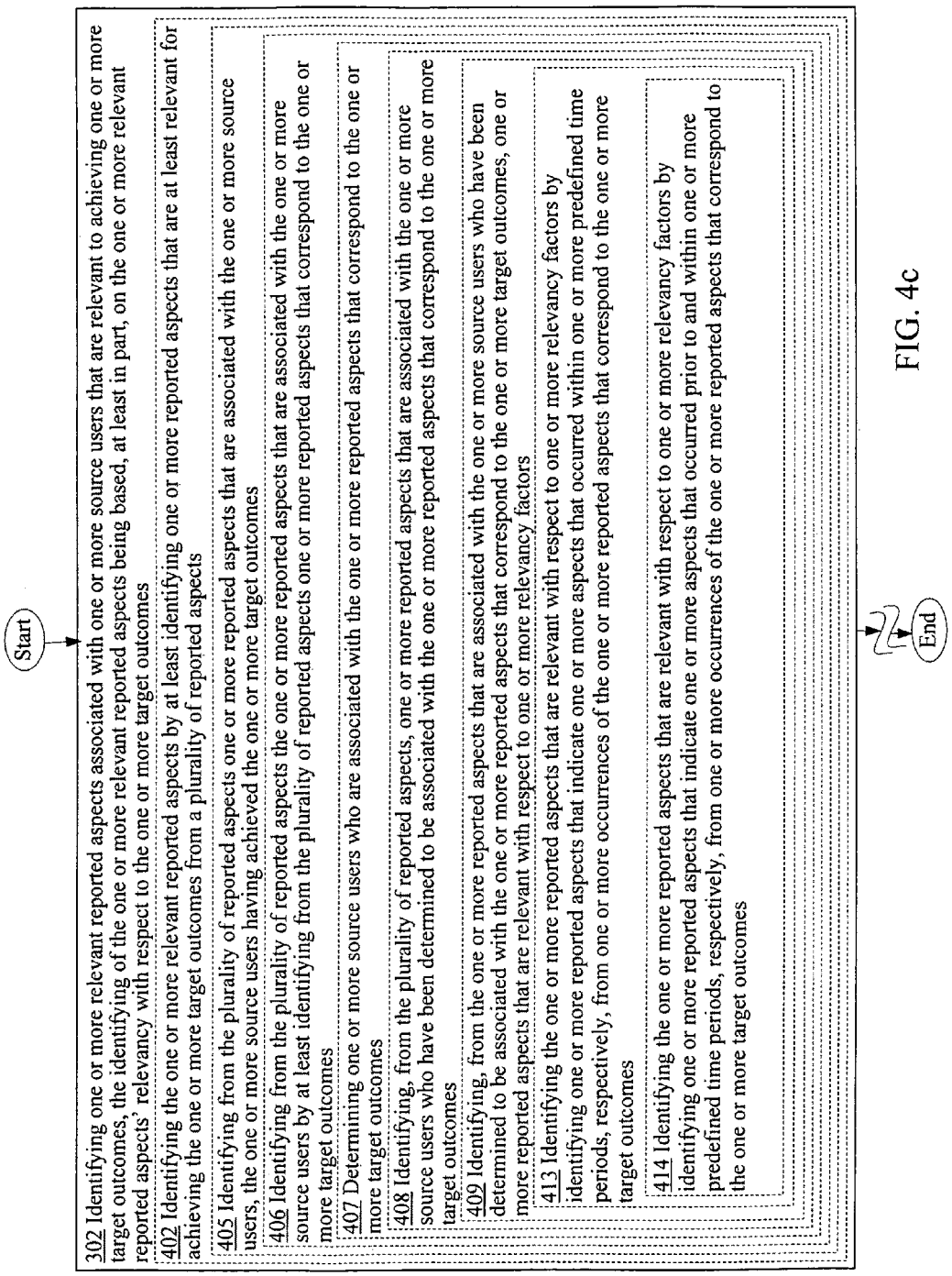
FIG. 4c is a high-level logic flowchart of a process depicting alternate implementations of the relevant reported aspect identifying operation 302 of FIG. 3.

In the same or different implementations, operation 409 may include an operation 413 for identifying the one or more reported aspects that are relevant with respect to one or more relevancy factors by identifying one or more reported aspects that indicate one or more aspects that occurred within one or more predefined time periods, respectively, from one or more occurrences of the one or more reported aspects that correspond to the one or more target outcomes as depicted in FIG. 4c. For instance, the relevancy factor relevant reported aspect identification module 208 of the computing device 10 identifying the one or more reported aspects 14 that are relevant with respect to one or more relevancy factors by identifying one or more reported aspects 14 that indicate one or more aspects that occurred within one or more predefined time periods, respectively, from one or more occurrences of the one or more reported aspects 14 that correspond to the one or more target outcomes.

That is, not all reported aspects 14 that are associated with the one or more source users 2* who have achieved the one or more target outcomes and that are relevant with respect to at least certain relevancy factors may actually be relevant to achieving the one or more target outcomes if the reported aspects 14 indicate aspects that, time-wise, occurred remotely from occurrence of the one or more target outcomes as successfully achieved by the one or more source users 2*. For example, reported aspects 14 that are associated with the one or more source users 2* who have achieved the one or more target outcomes and that are relevant based on certain relevancy factors (e.g., belonging to a type of aspect that is of interest to the end user 4) may, nevertheless, not be relevant to achieving the one or more target outcomes if they occurred well before (or well after) the achievement of the one or more target outcomes (e.g., as represented by one or more reported aspects that correspond to the one or more target outcomes) by the one or more source users 2*. Thus, a reported aspect 14 may, in some cases, be relevant to the achievement of the one or more target outcomes only if it falls within some time period (e.g., "predefined time period") from the one or more occurrences of the one or more reported aspects that correspond to the one or more target outcomes. The length of the predefined time periods to be considered in determining relevancy may depend on a number of factors.

For example, in some embodiments, the one or more predefined time periods (e.g., each of the one or more target outcomes may be associated with a different predefined time period) may be set based on the type of personalized plans 16 being developed. Alternatively, the one or more predefined time periods may be set by the end user 4, by one or more source users 2*, or by one or more third parties 6. As an illustration, suppose an end user 4 is interested in finding out what type of reading activities could help improve his verbal score on the SAT in six months. The end user 4 may then indicate that he is only interested in reported aspects 14 that indicate reading activities that have occurred during the six months prior to the taking of an SAT exam.

In some implementations, operation 413 may further include an operation 414 for identifying the one or more reported aspects that are relevant with respect to one or more relevancy factors by identifying one or more reported aspects that indicate one or more aspects that occurred prior to and within one or more predefined time periods, respectively, from one or more occurrences of the one or more reported aspects that correspond to the one or more target outcomes as depicted in FIG. 4c. For instance, the relevancy factor relevant reported aspect identification module 208 of the computing device 10 identifying the one or more reported aspects 14 that are relevant with respect to one or more relevancy factors by identifying one or more reported aspects 14 that indicate one or more aspects (e.g., exercise activities) that occurred prior to and within one or more predefined time periods (e.g., one month), respectively, from one or more occurrences of the one or more reported aspects 14 that correspond to the one or more target outcomes (e.g., 20 pound body weight loss). That is, generally in most (but not all) cases, reported aspects 14 that indicate aspects that are deemed to be relevant to achieving a particular target outcome will typically occur prior to the target outcome being achieved.

Figure 4D:
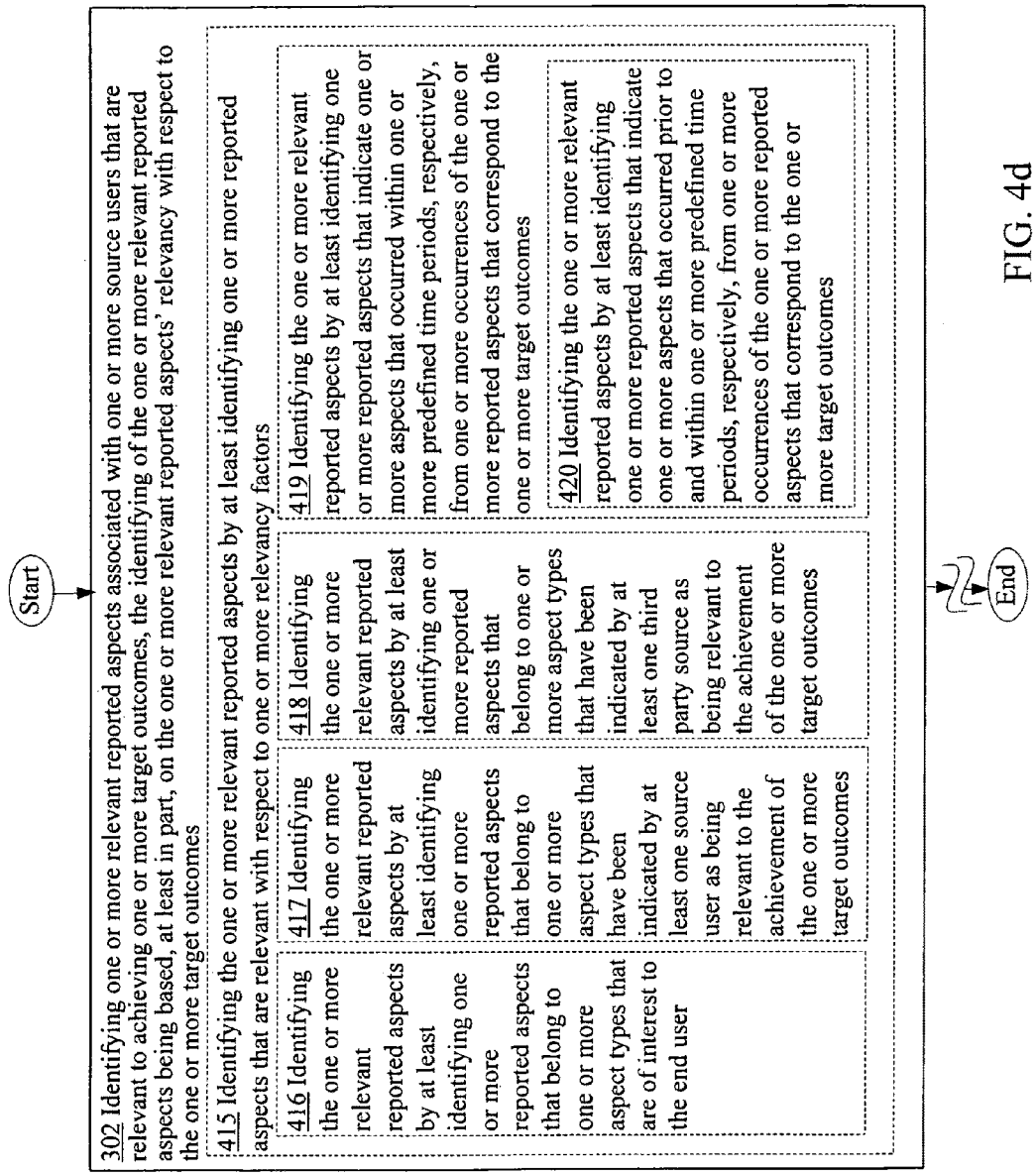
FIG. 4d is a high-level logic flowchart of a process depicting alternate implementations of the relevant reported aspect identifying operation 302 of FIG. 3.

In some implementations, the relevant reported aspect identifying operation 302 may not include a determination for the one or more source users 2* who may have achieved the one or more target outcomes. For these implementations, the relevant reported aspect identifying operation 302 may, nevertheless, include an operation 415 for identifying the one or more relevant reported aspects by at least identifying one or more reported aspects that are relevant with respect to one or more relevancy factors as depicted in FIG. 4d. For instance, the relevancy factor relevant reported aspect identification module 208 of the computing device 10 identifying the one or more relevant reported aspects by at least identifying one or more reported aspects 14 that are relevant with respect to one or more relevancy factors.

Operation 415 may in turn include one or more additional operations in various alternative implementations. For example, in some implementations, operation 415 may include an operation 416 for identifying the one or more relevant reported aspects by at least identifying one or more reported aspects that belong to one or more aspect types that are of interest to the end user as depicted in FIG. 4d. For instance, the relevancy factor relevant reported aspect identification module 208 of the computing device 10 identifying the one or more relevant reported aspects by at least identifying one or more reported aspects 14 that belong to one or more aspect types (e.g., conduct at workplace) that are of interest to the end user 4.

In the same or different implementations, operation 415 may include an operation 417 for identifying the one or more relevant reported aspects by at least identifying one or more reported aspects that belong to one or more aspect types that have been indicated by at least one source user as being relevant to the achievement of the one or more target outcomes as depicted in FIG. 4d. For instance, the relevancy factor relevant reported aspect identification module 208 of the computing device 10 identifying the one or more relevant reported aspects by at least identifying one or more reported aspects 14 that belong to one or more aspect types (e.g., caffeine consumption) that have been indicated by at least one source user 2* as being relevant to the achievement of the one or more target outcomes (e.g., having a relaxed temperament).

In the same or different implementations, operation 415 may include an operation 418 for identifying the one or more relevant reported aspects by at least identifying one or more reported aspects that belong to one or more aspect types that have been indicated by at least one third party source as being relevant to the achievement of the one or more target outcomes as depicted in FIG. 4d. For instance, the relevancy factor relevant reported aspect identification module 208 of the computing device 10 identifying the one or more relevant reported aspects by at least identifying one or more reported aspects 14 that belong to one or more aspect types (e.g., social activities) that have been indicated by at least one third party source (e.g., a third party 6, a publication, a content provider, and so forth) as being relevant to the achievement of the one or more target outcomes (e.g., having many friends).

In the same or different implementations, operation 415 may include an operation 419 for identifying the one or more relevant reported aspects by at least identifying one or more reported aspects that indicate one or more aspects that occurred within one or more predefined time periods, respectively, from one or more occurrences of the one or more reported aspects that correspond to the one or more target outcomes as depicted in FIG. 4d. For instance, the relevancy factor relevant reported aspect identification module 208 of the computing device 10 identifying the one or more relevant reported aspects by at least identifying one or more reported aspects 14 that indicate one or more aspects (e.g., caffeine consumption) that occurred within one or more predefined time periods (e.g., 24 hours), respectively, from one or more occurrences of the one or more reported aspects 14 that correspond to the one or more target outcomes (e.g., being alert at work).

In some implementations, operation 419 may further include an operation 420 for identifying the one or more relevant reported aspects by at least identifying one or more reported aspects that indicate one or more aspects that occurred prior to and within one or more predefined time periods, respectively, from one or more occurrences of the one or more reported aspects that correspond to the one or more target outcomes as depicted in FIG. 4d. For instance, the relevancy factor relevant reported aspect identification module 208 of the computing device 10 identifying the one or more relevant reported aspects by at least identifying one or more reported aspects 14 that indicate one or more aspects that occurred prior to and within one or more predefined time periods, respectively, from one or more occurrences of the one or more reported aspects 14 that correspond to the one or more target outcomes.

Figure 4E:
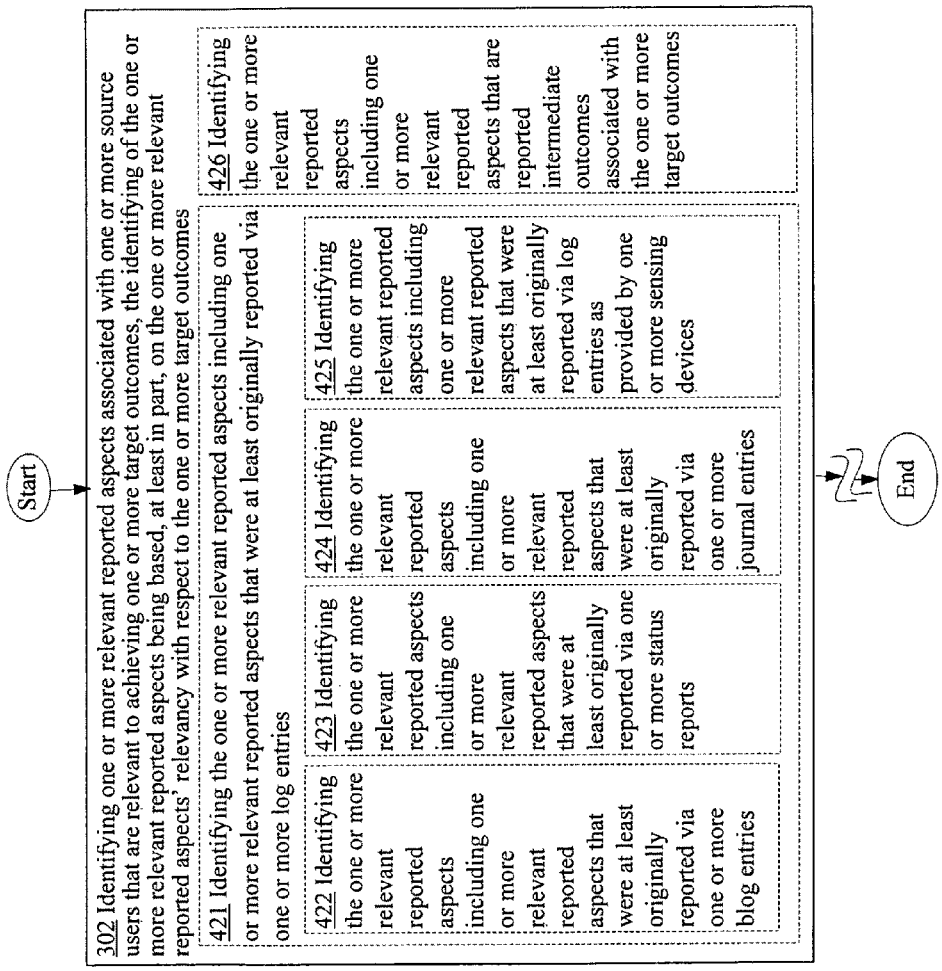
FIG. 4e is a high-level logic flowchart of a process depicting alternate implementations of the relevant reported aspect identifying operation 302 of FIG. 3.

The one or more relevant reported aspects to be identified via the relevant reported aspect identifying operation 302 of FIG. 3 may have been originally reported in a number of different ways. For example, in some implementations, the relevant reported aspect identifying operation 302 may include an operation 421 for identifying the one or more relevant reported aspects including one or more relevant reported aspects that were at least originally reported via one or more log entries as depicted in FIG. 4e. For instance, the relevancy factor relevant reported aspect identification module 208 of the computing device 10 identifying the one or more relevant reported aspects including one or more relevant reported aspects that were at least originally reported via one or more log entries. A log entry, as described here, may be any type of, for example, electronic entry that may be regularly, semi-regularly, or randomly entered by, for example, a source user 2*, a sensing device 40, or by a third party 6. A log entry, as will be further described herein, may come in a variety of different forms.

For example, in some implementations, operation 421 may include an operation 422 for identifying the one or more relevant reported aspects including one or more relevant reported aspects that were at least originally reported via one or more blog entries as depicted by FIG. 4e. For instance, the relevant reported aspect identification module 102 of the computing device 10 identifying the one or more relevant reported aspects including one or more relevant reported aspects that were at least originally reported via one or more blog entries (e.g., microblog entries).

In the same or different implementations, operation 421 may include an operation 423 for identifying the one or more relevant reported aspects including one or more relevant reported aspects that were at least originally reported via one or more status reports as depicted in FIG. 4e. For instance, the relevant reported aspect identification module 102 of the computing device 10 identifying the one or more relevant reported aspects including one or more relevant reported aspects that were at least originally reported via one or more status reports (e.g., social networking status reports).

In the same or different implementations, operation 421 may include an operation 424 for identifying the one or more relevant reported aspects including one or more relevant reported aspects that were at least originally reported via one or more journal entries as depicted in FIG. 4e. For instance, the relevant reported aspect identification module 102 of the computing device 10 identifying the one or more relevant reported aspects including one or more relevant reported aspects that were at least originally reported via one or more journal entries.

In the same or different implementations, operation 421 may include an operation 425 for identifying the one or more relevant reported aspects including one or more relevant reported aspects that were at least originally reported via log entries as provided by one or more sensing devices as depicted in FIG. 4e. For instance, the relevant reported aspect identification module 102 of the computing device 10 identifying the one or more relevant reported aspects including one or more relevant reported aspects that were at least originally reported via log entries as provided by one or more sensing devices 40 (e.g., sensing devices that can detect or sense source user activities or physiological characteristics of one or more source users 2*).

In some implementations, the relevant reported aspect identifying operation 302 of FIG. 3 may include an operation 426 for identifying the one or more relevant reported aspects including one or more relevant reported aspects that are reported intermediate outcomes associated with the one or more target outcomes as depicted in FIG. 4e. For instance, the relevant reported aspect identification module 102 of the computing device 10 identifying the one or more relevant reported aspects including one or more relevant reported aspects that are reported intermediate outcomes (e.g., losing 10 pounds of body weight) associated with the one or more target outcomes (e.g., losing 20 pounds of body weight).

In order to execute such an operation, operation 426 for identifying the one or more relevant reported aspects that are reported intermediate outcomes may include one or more additional operations such as initially identifying the one or more source users 2* who have achieved the one or more target outcomes, and identifying reported aspects 14 associated with the one or more source users 2* who have achieved the one or more target outcomes and that may be intermediate reported outcomes associated with the one or more target outcomes. Note that when developing the one or more personalized plans 16, one or more emulatable intermediate outcomes that correspond to the reported intermediate outcomes may be included into the one or more personalized plans 16. In doing so, the end user 4 may be better facilitated in tracking his/her progress towards achieving, for example, the desired target outcomes.

Figure 4F:
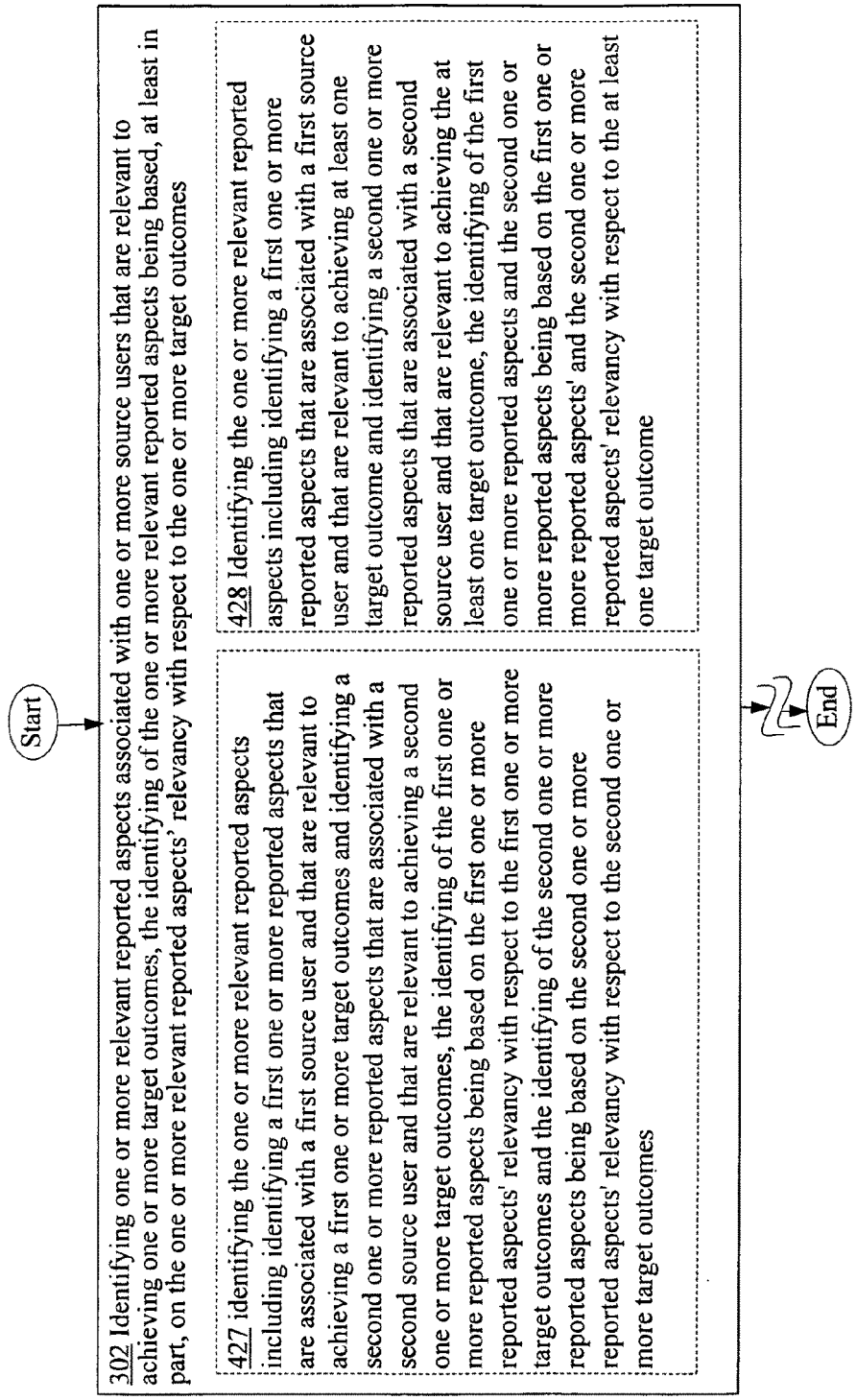
FIG. 4f is a high-level logic flowchart of a process depicting alternate implementations of the relevant reported aspect identifying operation 302 of FIG. 3.

In some cases, the relevant reported aspect identifying operation 302 of FIG. 3 may involve identifying relevant reported aspects that are associated with multiple source users 2*. For example, in some implementations, the relevant reported aspect identifying operation 302 of FIG. 3 may include an operation 427 for identifying the one or more relevant reported aspects including identifying a first one or more reported aspects that are associated with a first source user and that are relevant to achieving a first one or more target outcomes and identifying a second one or more reported aspects that are associated with a second source user and that are relevant to achieving a second one or more target outcomes, the identifying of the first one or more reported aspects being based on the first one or more reported aspects' relevancy with respect to the first one or more target outcomes and the identifying of the second one or more reported aspects being based on the second one or more reported aspects' relevancy with respect to the second one or more target outcomes as depicted in FIG. 4f. For instance, the relevant reported aspect identification module 102 of the computing device 10 identifying the one or more relevant reported aspects including identifying a first one or more reported aspects 14 that are associated with a first source user 2a and that are relevant to achieving a first one or more target outcomes and identifying a second one or more reported aspects 14 that are associated with a second source user 2b and that are relevant to achieving a second one or more target outcomes, the identifying of the first one or more reported aspects 14 being based on the first one or more reported aspects' relevancy with respect to the first one or more target outcomes and the identifying of the second one or more reported aspects 14 being based on the second one or more reported aspects' relevancy with respect to the second one or more target outcomes.

In the same or different implementations, the relevant reported aspect identifying operation 302 may include an operation 428 for identifying the one or more relevant reported aspects including identifying a first one or more reported aspects that are associated with a first source user and that are relevant to achieving at least one target outcome and identifying a second one or more reported aspects that are associated with a second source user and that are relevant to achieving the at least one target outcome, the identifying of the first one or more reported aspects and the second one or more reported aspects being based on the first one or more reported aspects' and the second one or more reported aspects' relevancy with respect to the at least one target outcome as depicted in FIG. 4f. For instance, the relevant reported aspect identification module 102 of the computing device 10 identifying the one or more relevant reported aspects including identifying a first one or more reported aspects 14 that are associated with a first source user 2a and that are relevant to achieving at least one target outcome and identifying a second one or more reported aspects 14 that are associated with a second source user 2b and that are relevant to achieving the at least one target outcome, the identifying of the first one or more reported aspects 14 and the second one or more reported aspects 14 being based on the first one or more reported aspects' and the second one or more reported aspects' relevancy with respect to the at least one target outcome.

Figure 4G:
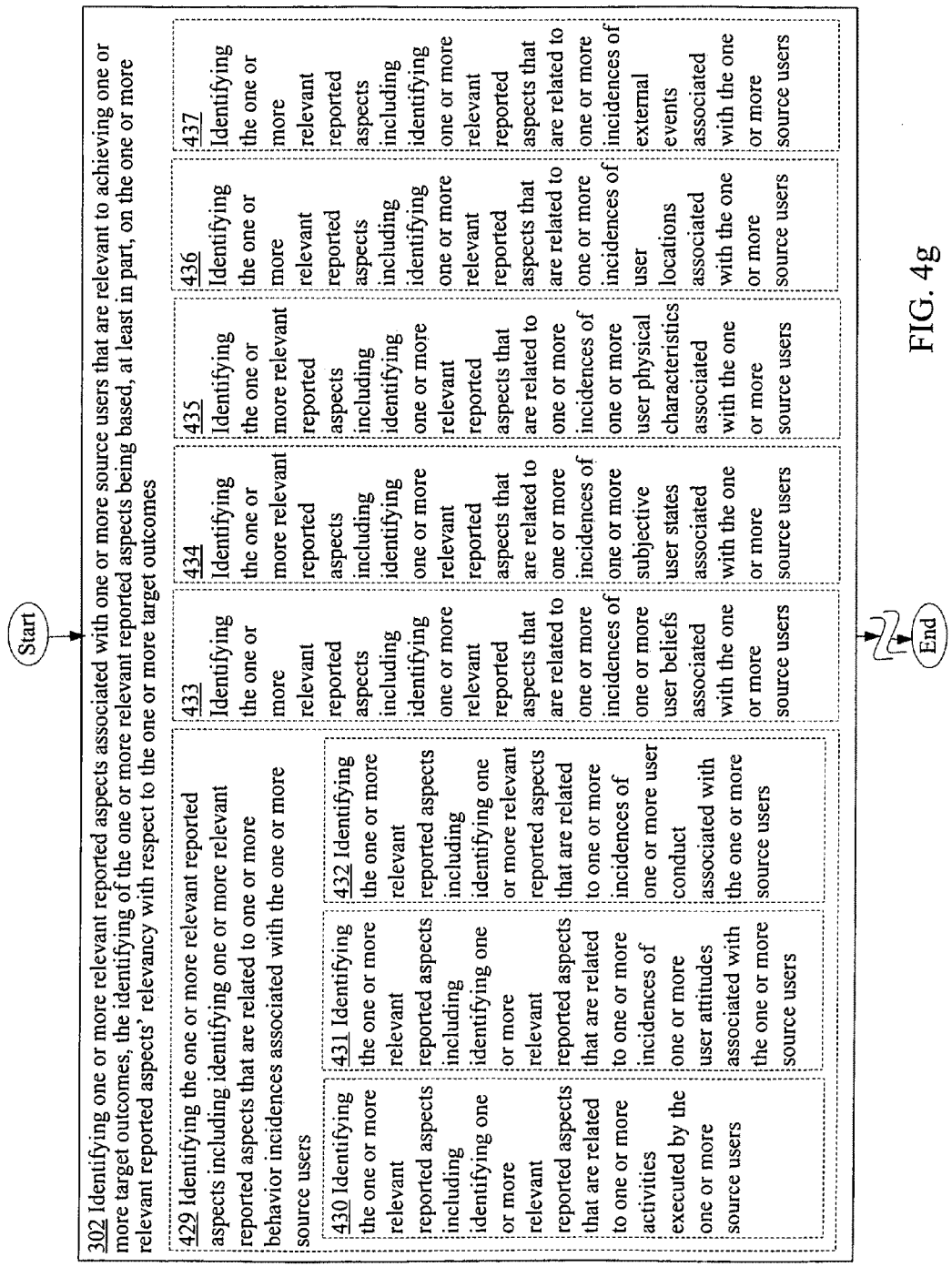
FIG. 4g is a high-level logic flowchart of a process depicting alternate implementations of the relevant reported aspect identifying operation 302 of FIG. 3.

Various types of aspects may be indicated by the one or more relevant reported aspects identified by the relevant reported aspect identifying operation 302 of FIG. 3 in various alternative implementations. For example, in some implementations, the relevant reported aspect identifying operation 302 may include an operation 429 for identifying the one or more relevant reported aspects including identifying one or more relevant reported aspects that are related to one or more behavior incidences associated with the one or more source users as depicted in FIG. 4g. For instance, the relevant reported aspect identification module 102 of the computing device 10 identifying the one or more relevant reported aspects including identifying one or more relevant reported aspects that are related to one or more behavior incidences associated with the one or more source users 2*.

Various types of behavior incidences may be indicated by the one or more relevant reported aspects identified by operation 429. For example, in some implementations, operation 429 may include an operation 430 for identifying the one or more relevant reported aspects including identifying one or more relevant reported aspects that are related to one or more activities executed by the one or more source users as depicted in FIG. 4g. For instance, the relevant reported aspect identification module 102 of the computing device 10 identifying the one or more relevant reported aspects including identifying one or more relevant reported aspects that are related to one or more activities (e.g., food or medicine ingestion activities, rest activities, occupational activities, exercise activities, social activities, and so forth) executed by the one or more source users 2*.

In the same or different implementations, operation 429 may include an operation 431 for identifying the one or more relevant reported aspects including identifying one or more relevant reported aspects that are related to one or more incidences of one or more user attitudes associated with the one or more source users as depicted in FIG. 4g. For instance, the relevant reported aspect identification module 102 of the computing device 10 identifying the one or more relevant reported aspects including identifying one or more relevant reported aspects that are related to one or more incidences of one or more user attitudes (e.g., being indifferent, feeling critical, feeling skeptical, feeling optimistic, and so forth) associated with the one or more source users 2*.

In the same or different implementations, operation 429 may include an operation 432 for identifying the one or more relevant reported aspects including identifying one or more relevant reported aspects that are related to one or more incidences of one or more user conduct associated with the one or more source users as depicted in FIG. 4g. For instance, the relevant reported aspect identification module 102 of the computing device 10 identifying the one or more relevant reported aspects including identifying one or more relevant reported aspects that are related to one or more incidences of one or more user conduct (e.g., behavior towards others, treatment of others, manner in which acts are executed, and so forth) associated with the one or more source users 2*.

Other types of relevant reported aspects other than those that indicate behavior incidences may be identified through the relevant reported aspect identifying operation 302 of FIG. 3 in various alternative implementations. For example, in some implementations, the relevant reported aspect identifying operation 302 may include an operation 433 for identifying the one or more relevant reported aspects including identifying one or more relevant reported aspects that are related to one or more incidences of one or more user beliefs associated with the one or more source users as depicted in FIG. 4g. For instance, the relevant reported aspect identification module 102 of the computing device 10 identifying the one or more relevant reported aspects including identifying one or more relevant reported aspects that are related to one or more incidences of one or more user beliefs (e.g., religious beliefs, spiritual beliefs, prejudicial beliefs, political beliefs, and so forth) associated with the one or more source users 2*.

In the same or different implementations, the relevant reported aspect identifying operation 302 may include an operation 434 for identifying the one or more relevant reported aspects including identifying one or more relevant reported aspects that are related to one or more incidences of one or more subjective user states associated with the one or more source users as depicted in FIG. 4g. For instance, the relevant reported aspect identification module 102 of the computing device 10 identifying the one or more relevant reported aspects including identifying one or more relevant reported aspects that are related to one or more incidences of one or more subjective user states associated with the one or more source users 2*.

A subjective user state may be any state or status associated with a source user 2* that can typically only be indicated by the source user 2*. Examples of subjective user states include, for example, subjective user mental states (e.g., sadness, happiness, mental exhaustion, alertness, and so forth), subjective user physical states (e.g., sore back, blurred vision, overall physical exhaustion, and so forth), and subjective user overall states (e.g., any other subjective user states that are neither a subjective user mental state or a subjective user physical state including, for example, "feeling good," "feeling bad," "feeling alive," and so forth).

In the same or different implementations, the relevant reported aspect identifying operation 302 may include an operation 435 for identifying the one or more relevant reported aspects including identifying one or more relevant reported aspects that are related to one or more incidences of one or more user physical characteristics associated with the one or more source users as depicted in FIG. 4g. For instance, the relevant reported aspect identification module 102 of the computing device 10 identifying the one or more relevant reported aspects including identifying one or more relevant reported aspects that are related to one or more incidences of one or more user physical characteristics (e.g., hair or eye color, hair length, hair style, facial hair characteristics, overall body figure, body weight, and so forth) associated with the one or more source users 2*.

In the same or different implementations, the relevant reported aspect identifying operation 302 may include an operation 436 for identifying the one or more relevant reported aspects including identifying one or more relevant reported aspects that are related to one or more incidences of user locations associated with the one or more source users as depicted in FIG. 4g. For instance, the relevant reported aspect identification module 102 of the computing device 10 identifying the one or more relevant reported aspects including identifying one or more relevant reported aspects that are related to one or more incidences of user locations (e.g., nightclub, football stadium, home residence, workplace, and so forth) associated with the one or more source users 2*.

In the same or different implementations, the relevant reported aspect identifying operation 302 may include an operation 437 for identifying the one or more relevant reported aspects including identifying one or more relevant reported aspects that are related to one or more incidences of external events associated with the one or more source users as depicted in FIG. 4g. For instance, the relevant reported aspect identification module 102 of the computing device 10 identifying the one or more relevant reported aspects including identifying one or more relevant reported aspects that are related to one or more incidences of external events (e.g., weather conditions, heavy or no road traffic, performance of one or more investment stocks that are of interest to the one or more source users 2*, and so forth) associated with the one or more source users 2*.

Figure 4H:
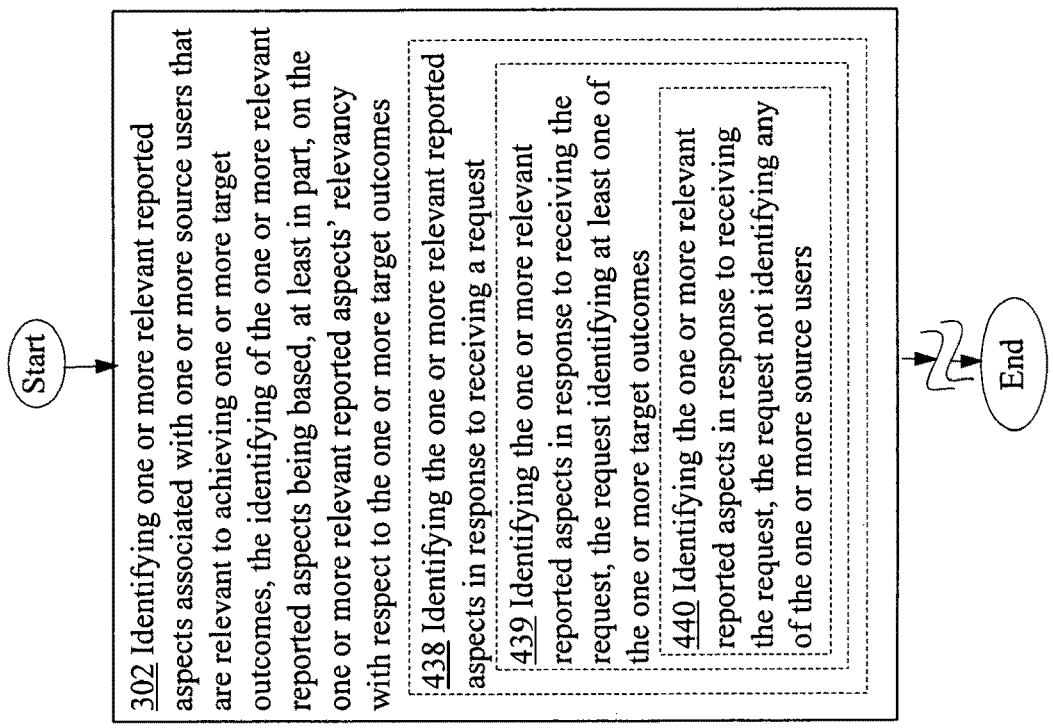
FIG. 4h is a high-level logic flowchart of a process depicting alternate implementations of the relevant reported aspect identifying operation 302 of FIG. 3.

In various implementations, the relevant reported aspect identifying operation 302 (as well as the operational flow 300) of FIG. 3 may be prompted when, for example, a request 12 is received. For example, in some implementations, the relevant reported aspect identifying operation 302 may include an operation 438 for identifying the one or more relevant reported aspects in response to receiving a request as depicted in FIG. 4h. For instance, the relevant reported aspect identification module 102 of the computing device 10 identifying the one or more relevant reported aspects in response to receiving a request 12 (e.g., a request 12 for the one or more personalized plans 16 as made by the end user 4 or by a third party 6). In the case where the computing device 10 is an end user device (e.g., local end user device 30) or a source user device (e.g., local source user device 20), the request 12 may be received through a user interface 120 or through a network interface 118. In the case where the computing device 10 is a server (e.g., network server 60), the request 12 may be received through the network interface 118.

In some implementations, operation 438 may further include an operation 439 for identifying the one or more relevant reported aspects in response to receiving the request, the request identifying at least one of the one or more target outcomes as depicted in FIG. 4h. For instance, the relevant reported aspect identification module 102 of the computing device 10 identifying the one or more relevant reported aspects in response to receiving the request 12, the request 12 identifying at least one of the one or more target outcomes.

In some cases, operation 439 may further include an operation 440 for identifying the one or more relevant reported aspects in response to receiving the request, the request not identifying any of the one or more source users as depicted in FIG. 4h. For instance, the relevant reported aspect identification module 102 of the computing device 10 identifying the one or more relevant reported aspects in response to receiving the request 12, the request 12 not identifying any of the one or more source users 2*. For example, if the requester (e.g., end user 4) is unaware of which user (e.g., source user 2*) may have achieved the one or more target outcomes, than the request 12 may not identify the one or more source users 2*.

Figure 5A:
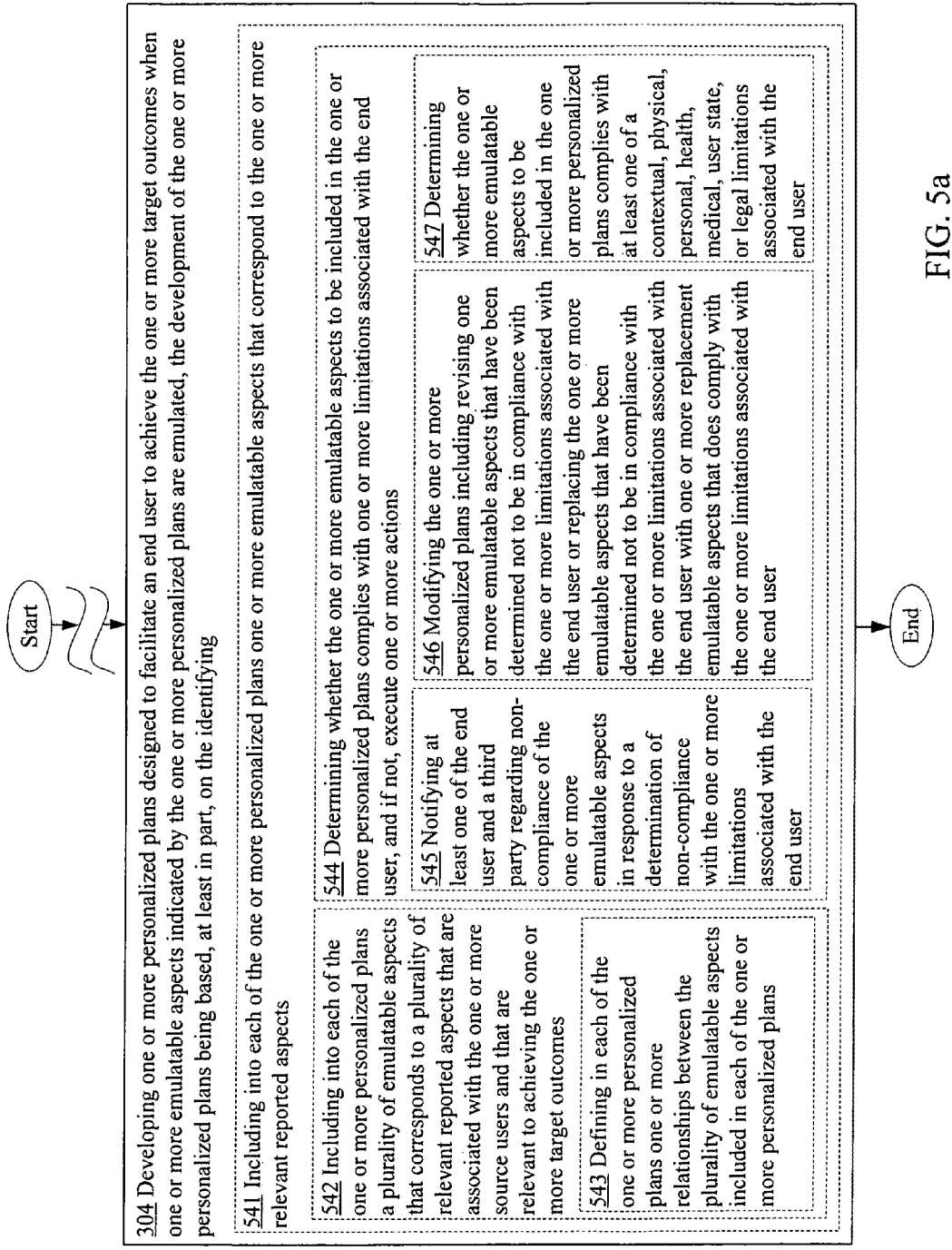
FIG. 5a is a high-level logic flowchart of a process depicting alternate implementations of the personalized plan developing operation 304 of FIG. 3.

Referring back to the personalized plan developing operation 304 of FIG. 3, the personalized plan developing operation 304 may include one or more additional operations in various implementations. For example, in some implementations, the personalized plan developing operation 304 may include an operation 541 for including into each of the one or more personalized plans one or more emulatable aspects that correspond to the one or more relevant reported aspects as depicted in FIG. 5a. For instance, the emulatable aspect inclusion module 220 (see FIG. 2b) of the computing device 10 including into each of the one or more personalized plans 16 one or more emulatable aspects that correspond to the one or more relevant reported aspects (e.g., as identified through the relevant reported aspect identifying operation 302).

In some cases, operation 541 may further include an operation 542 for including into each of the one or more personalized plans a plurality of emulatable aspects that corresponds to a plurality of relevant reported aspects that are associated with the one or more source users and that are relevant to achieving the one or more target outcomes as depicted in FIG. 5a. For instance, the emulatable aspect inclusion module 220 of the computing device 10 including into each of the one or more personalized plans 16 a plurality of emulatable aspects that corresponds to a plurality of relevant reported aspects that are associated with the one or more source users 2* and that are relevant to achieving the one or more target outcomes.

In turn, operation 542 may include, in various implementations, an operation 543 for defining in each of the one or more personalized plans one or more relationships between the plurality of emulatable aspects included in each of the one or more personalized plans as depicted in FIG. 5a. For instance, the relationship defining module 222 (see FIG. 2b) of the computing device 10 defining in each of the one or more personalized plans 16 one or more relationships (e.g., temporal relationships, specific time relationships, and/or spatial relationships) between the plurality of emulatable aspects included in each of the one or more personalized plans 16.

In various implementations, the operation 541 for including into each of the one or more personalized plans one or more emulatable aspects that correspond to the one or more relevant reported aspects may include an operation 544 for determining whether the one or more emulatable aspects to be included in the one or more personalized plans complies with one or more limitations associated with the end user, and if not, execute one or more actions as depicted in FIG. 5a. For instance, the limitation compliance determination module 224 (see FIG. 2b) of the computing device 10 determining whether the one or more emulatable aspects to be included in the one or more personalized plans 16 complies with (e.g., does not violate) one or more limitations associated with the end user 4 (e.g., limitations that prevent or make it impractical for the one or more emulatable aspects to be successfully emulated), and if not compliant, execute one or more actions.

In various implementations, operation 544 may further include one or more additional operations. For example, in some implementations, operation 544 may include an operation 545 for notifying at least one of the end user and a third party regarding non-compliance of the one or more emulatable aspects in response to a determination of non-compliance with the one or more limitations associated with the end user as depicted in FIG. 5a. For instance, the non-compliance notification module 226 (see FIG. 2b) of the computing device 10 notifying at least one of the end user 4 and a third party 6 regarding non-compliance of the one or more emulatable aspects in response to a determination of non-compliance with the one or more limitations associated with the end user 4.

In the same or different implementations, operation 544 may include an operation 546 for modifying the one or more personalized plans including revising one or more emulatable aspects that have been determined not to be in compliance with the one or more limitations associated with the end user or replacing the one or more emulatable aspects that have been determined not to be in compliance with the one or more limitations associated with the end user with one or more replacement emulatable aspects that does comply with the one or more limitations associated with the end user as depicted in FIG. 5a. For instance, the personalized plan modification module 228 (see FIG. 2b) of the computing device 10 modifying the one or more personalized plans 16 including revising one or more emulatable aspects that have been determined not to be in compliance with the one or more limitations associated with the end user 4 or replacing the one or more emulatable aspects that have been determined not to be in compliance with the one or more limitations associated with the end user 4 with one or more replacement emulatable aspects that does comply with the one or more limitations associated with the end user 4. As a further illustration, if an emulatable aspect such as "swimming for 40 minutes" is determined to be non-compliant, than replacing the non-compliant emulatable aspect with a complaint emulatable aspect (e.g., "jogging for one hour" that results in the same amount of calories being burned) that is at least proximately equivalent to the non-compliant emulatable aspect. Of course, what is "at least proximately equivalent" will depend on the type of emulatable aspect being replaced and the type of personalized plan 16 being developed.

In the same or different implementations, operation 544 may include an operation 547 for determining whether the one or more emulatable aspects to be included in the one or more personalized plans complies with at least one of a contextual, physical, personal, health, medical, user state, or legal limitations associated with the end user as depicted in FIG. 5a. For instance, the limitation compliance determination module 224 of the computing device 10 determining whether the one or more emulatable aspects to be included in the one or more personalized plans 16 complies with at least one of a contextual (e.g., logistical limitations such as scheduling limitations, geographical limitations, asset limitations, and so forth), physical (e.g., missing limb, paralysis, visual or hearing impediment, and so forth), personal (e.g., religious beliefs, dietary beliefs, phobias, personal prejudices, limitations related to personal experiences, personal work schedule obligations, family dynamics or circumstances, and so forth), health or medical (e.g., medical limitations such as limitations resulting from an illness or treatment of an illness including limitations due to cancer or treatment of the cancer, health limitations related to the physical conditioning of the end user 4, genetic limitations, and so forth), user state (e.g., end user 4 is married, end user 4 is in mourning, end user 4 is unemployed, end user 4 is a vegan, and so forth), or legal limitations (e.g., drug regulations, laws related to conduct or behavior in the jurisdiction of the end user 4, and so forth) associated with the end user 4, and if not, execute one or more actions.

Figure 5B:
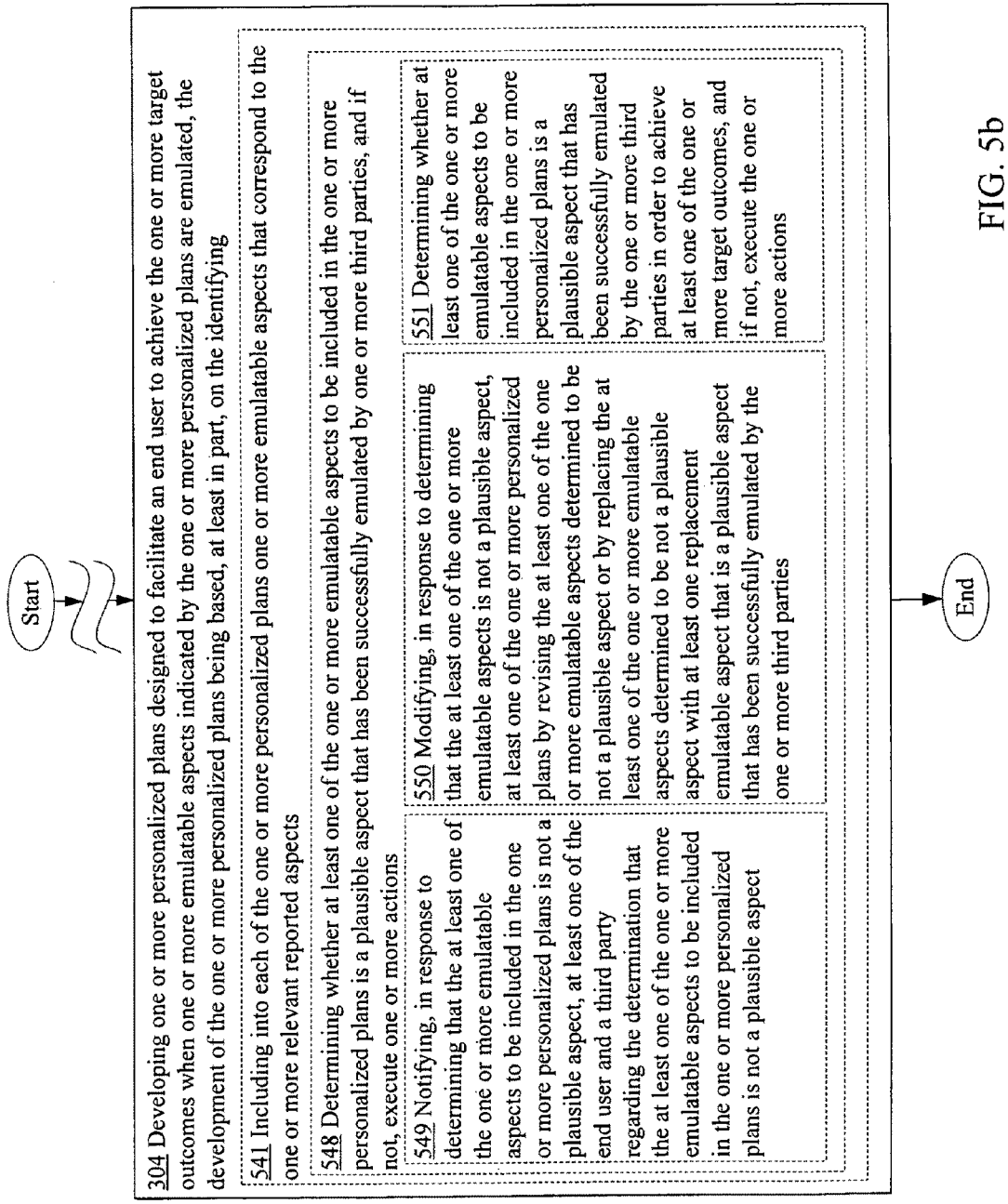
FIG. 5b is a high-level logic flowchart of a process depicting alternate implementations of the personalized plan developing operation 304 of FIG. 3.

In various implementations, the operation 541 for including one or more emulatable aspects into each of the one or more personalized plans may include an operation 548 for determining whether at least one of the one or more emulatable aspects to be included in the one or more personalized plans is a plausible aspect that has been successfully emulated by one or more third parties, and if not, execute one or more actions as depicted in FIG. 5b. For instance, the plausible determination module 230 (see FIG. 2b) of the computing device 10 determining whether at least one of the one or more emulatable aspects to be included in the one or more personalized plans 16 is a plausible aspect that has been successfully emulated by one or more third parties 6 (e.g., other end users 4* or disinterested parties), and if not plausible, execute one or more actions.

In various alternative implementations, operation 548 may include one or more additional operations. For example, in some implementations, operation 548 may include an operation 549 for notifying, in response to determining that the at least one of the one or more emulatable aspects to be included in the one or more personalized plans is not a plausible aspect, at least one of the end user and a third party regarding the determination that the at least one of the one or more emulatable aspects to be included in the one or more personalized plans is not a plausible aspect as depicted in FIG. 5b. For instance, the not plausible notification module 234 (see FIG. 2b) of computing device 10 notifying, in response to determining that the at least one of the one or more emulatable aspects to be included in the one or more personalized plans 16 is not a plausible aspect, at least one of the end user 4 and a third party 6 regarding the determination that the at least one of the one or more emulatable aspects to be included in the one or more personalized plans 16 is not a plausible aspect.

In the same or different implementations, operation 548 may include an operation 550 for modifying, in response to determining that the at least one of the one or more emulatable aspects is not a plausible aspect, at least one of the one or more personalized plans by revising the at least one of the one or more emulatable aspects determined to be not a plausible aspect or by replacing the at least one of the one or more emulatable aspects determined to be not a plausible aspect with at least one replacement emulatable aspect that is a plausible aspect that has been successfully emulated by the one or more third parties as depicted in FIG. 5b. For instance, the personalized plan modification module 236 (see FIG. 2b) of the computing device 10 modifying, in response to determining that the at least one of the one or more emulatable aspects is not a plausible aspect, at least one of the one or more personalized plans 16 by revising the at least one of the one or more emulatable aspects determined to be not a plausible aspect or by replacing the at least one of the one or more emulatable aspects determined to be not a plausible aspect with at least one replacement emulatable aspect that is a plausible aspect that has been successfully emulated by one or more third parties 6 (e.g., other end users 4* or disinterested parties).

In the same or different implementations, operation 548 may include an operation 551 for determining whether at least one of the one or more emulatable aspects to be included in the one or more personalized plans is a plausible aspect that has been successfully emulated by the one or more third parties in order to achieve at least one of the one or more target outcomes, and if not, execute the one or more actions as depicted in FIG. 5b. For instance, the plausible determination module 230 of the computing device 10 determining whether at least one of the one or more emulatable aspects to be included in the one or more personalized plans 16 is a plausible aspect that has been successfully emulated by one or more third parties 6 in order to achieve at least one of the one or more target outcomes, and if not plausible, execute one or more actions.

Figure 5C:
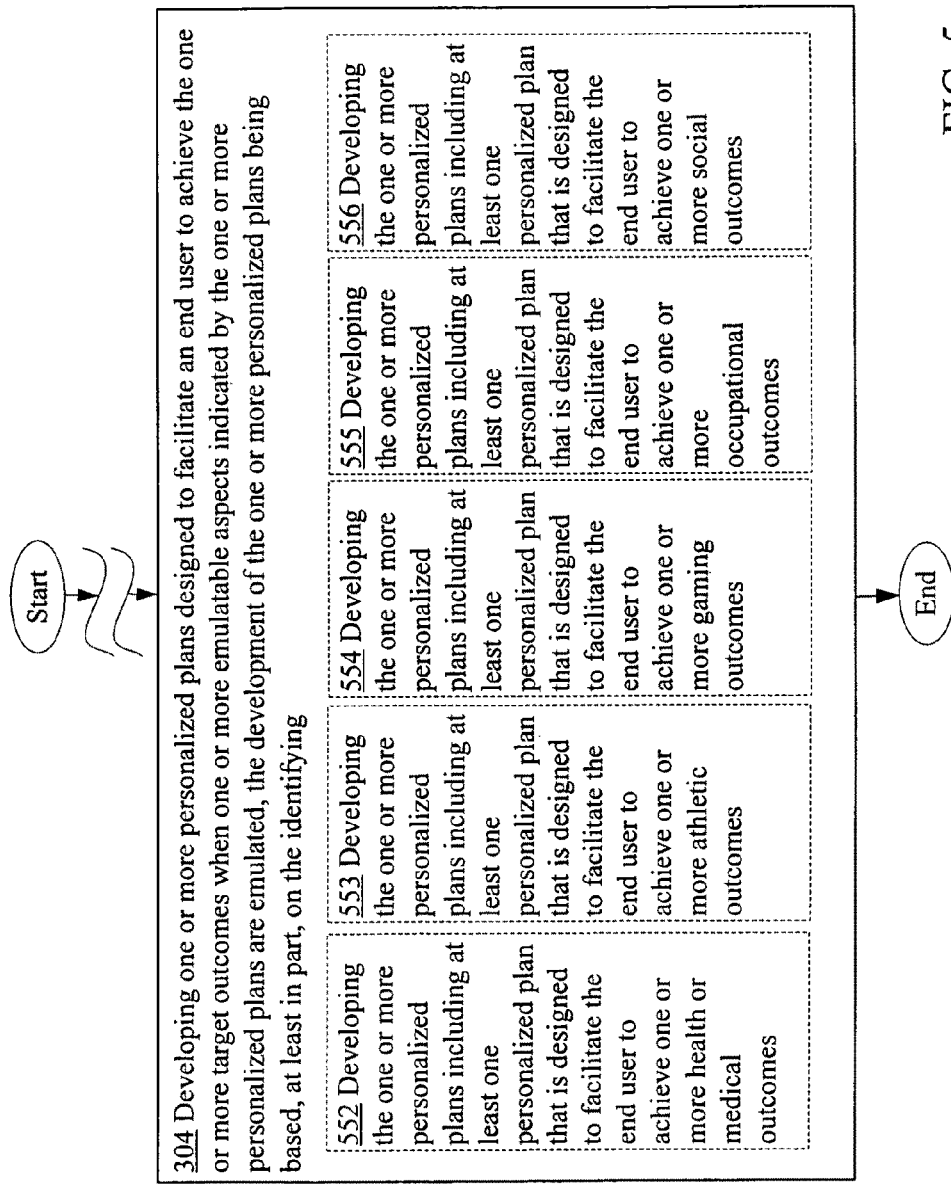
FIG. 5c is a high-level logic flowchart of a process depicting alternate implementations of the personalized plan developing operation 304 of FIG. 3.

Various types of personalized plans 16 may be developed through the personalized plan developing operation 304 of FIG. 3. For example, in some implementations, the personalized plan developing operation 304 may include an operation 552 for developing the one or more personalized plans including at least one personalized plan that is designed to facilitate the end user to achieve one or more health or medical outcomes as depicted in FIG. 5c. For instance, the personalized plan development module 104 of the computing device 10 developing the one or more personalized plans 16 including at least one personalized plan 16 that is designed to facilitate the end user 4 to achieve one or more health or medical outcomes (e.g., recovery time or recovery success related to an illness, weight loss, improve lifespan, physiological outcomes such as reducing blood pressure or blood glucose levels, increase red blood cell count, improve blood circulation, and so forth).

In the same or different implementations, the personalized plan developing operation 304 may include an operation 553 for developing the one or more personalized plans including at least one personalized plan that is designed to facilitate the end user to achieve one or more athletic outcomes as depicted in FIG. 5c. For instance, the personalized plan development module 104 of the computing device 10 developing the one or more personalized plans 16 including at least one personalized plan 16 that is designed to facilitate the end user 4 to achieve one or more athletic outcomes (e.g., improve golf scores, win a bicycle or swimming race, develop a curve ball pitch, and so forth).

In the same or different implementations, the personalized plan developing operation 304 may include an operation 554 for developing the one or more personalized plans including at least one personalized plan that is designed to facilitate the end user to achieve one or more gaming outcomes as depicted in FIG. 5c. For instance, the personalized plan development module 104 of the computing device 10 developing the one or more personalized plans 16 including at least one personalized plan 16 that is designed to facilitate the end user 4 to achieve one or more gaming outcomes (e.g., winning a chest tournament or improve video gaming skills).

In the same or different implementations, the personalized plan developing operation 304 may include an operation 555 for developing the one or more personalized plans including at least one personalized plan that is designed to facilitate the end user to achieve one or more occupational outcomes as depicted in FIG. 5c. For instance, the personalized plan development module 104 of the computing device 10 developing the one or more personalized plans 16 including at least one personalized plan 16 that is designed to facilitate the end user 4 to achieve one or more occupational outcomes (e.g., a job promotion, complete a work project on time, develop new occupational relationships, and so forth).

In the same or different implementations, the personalized plan developing operation 304 may include an operation 556 for developing the one or more personalized plans including at least one personalized plan that is designed to facilitate the end user to achieve one or more social outcomes as depicted in FIG. 5c. For instance, the personalized plan development module 104 of the computing device 10 developing the one or more personalized plans 16 including at least one personalized plan 16 that is designed to facilitate the end user 4 to achieve one or more social outcomes (e.g., attaining a certain social class, having a dinner date with a particular person, developing a particular reputation, develop or expand social networks, and so forth).

Figure 5D:
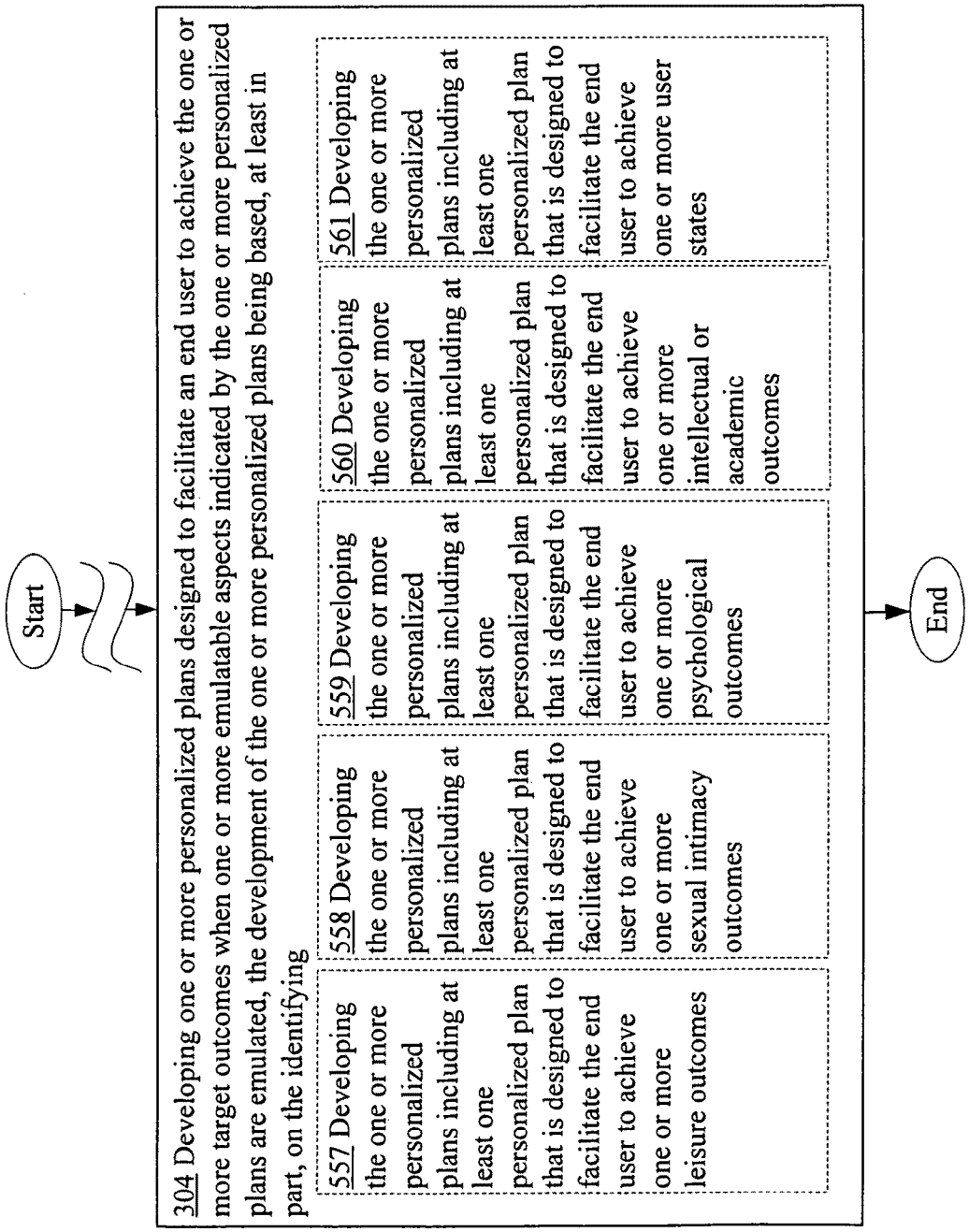
FIG. 5d is a high-level logic flowchart of a process depicting alternate implementations of the personalized plan developing operation 304 of FIG. 3.

In the same or different implementations, the personalized plan developing operation 304 may include an operation 557 for developing the one or more personalized plans including at least one personalized plan that is designed to facilitate the end user to achieve one or more leisure outcomes as depicted in FIG. 5d. For instance, the personalized plan development module 104 of the computing device 10 developing the one or more personalized plans 16 including at least one personalized plan that is designed to facilitate the end user 4 to achieve one or more leisure outcomes (e.g., learn how to knit, finding time to go on vacation, finish reading a book, and so forth).

In the same or different implementations, the personalized plan developing operation 304 may include an operation 558 for developing the one or more personalized plans including at least one personalized plan that is designed to facilitate the end user to achieve one or more sexual intimacy outcomes as depicted in FIG. 5d. For instance, the personalized plan development module 104 of the computing device 10 developing the one or more personalized plans 16 including at least one personalized plan 16 that is designed to facilitate the end user 4 to achieve one or more sexual intimacy outcomes (e.g., increased sexual activities, increased sexual performance, and so forth).

In the same or different implementations, the personalized plan developing operation 304 may include an operation 559 for developing the one or more personalized plans including at least one personalized plan that is designed to facilitate the end user to achieve one or more psychological outcomes as depicted in FIG. 5d. For instance, the personalized plan development module 104 of the computing device 10 developing the one or more personalized plans 16 including at least one personalized plan 16 that is designed to facilitate the end user 4 to achieve one or more psychological outcomes (e.g., overcoming a phobia, overcoming certain addictive behavior such as compulsion to be clean, and so forth).

In the same or different implementations, the personalized plan developing operation 304 may include an operation 560 for developing the one or more personalized plans including at least one personalized plan that is designed to facilitate the end user to achieve one or more intellectual or academic outcomes as depicted in FIG. 5d. For instance, the personalized plan development module 104 of the computing device 10 developing the one or more personalized plans 16 including at least one personalized plan 16 that is designed to facilitate the end user 4 to achieve one or more intellectual or academic outcomes (e.g., passing a particular exam or class, obtaining a certain degree or academic award, being accepted into a particular program or school, attaining a particular scholarship, understanding a complex concept, acquiring particular knowledge, and so forth).

In the same or different implementations, the personalized plan developing operation 304 may include an operation 561 for developing the one or more personalized plans including at least one personalized plan that is designed to facilitate the end user to achieve one or more user states as depicted in FIG. 5d. For instance, the personalized plan development module 104 of the computing device 10 developing the one or more personalized plans 16 including at least one personalized plan 16 that is designed to facilitate the end user 4 to achieve one or more user states (e.g., subjective user states such as subjective mental, physical, and/or overall states, marital states, occupational states, physical states, availability states, social states, spiritual or faith-based states, academic states, and so forth).

Figure 6:
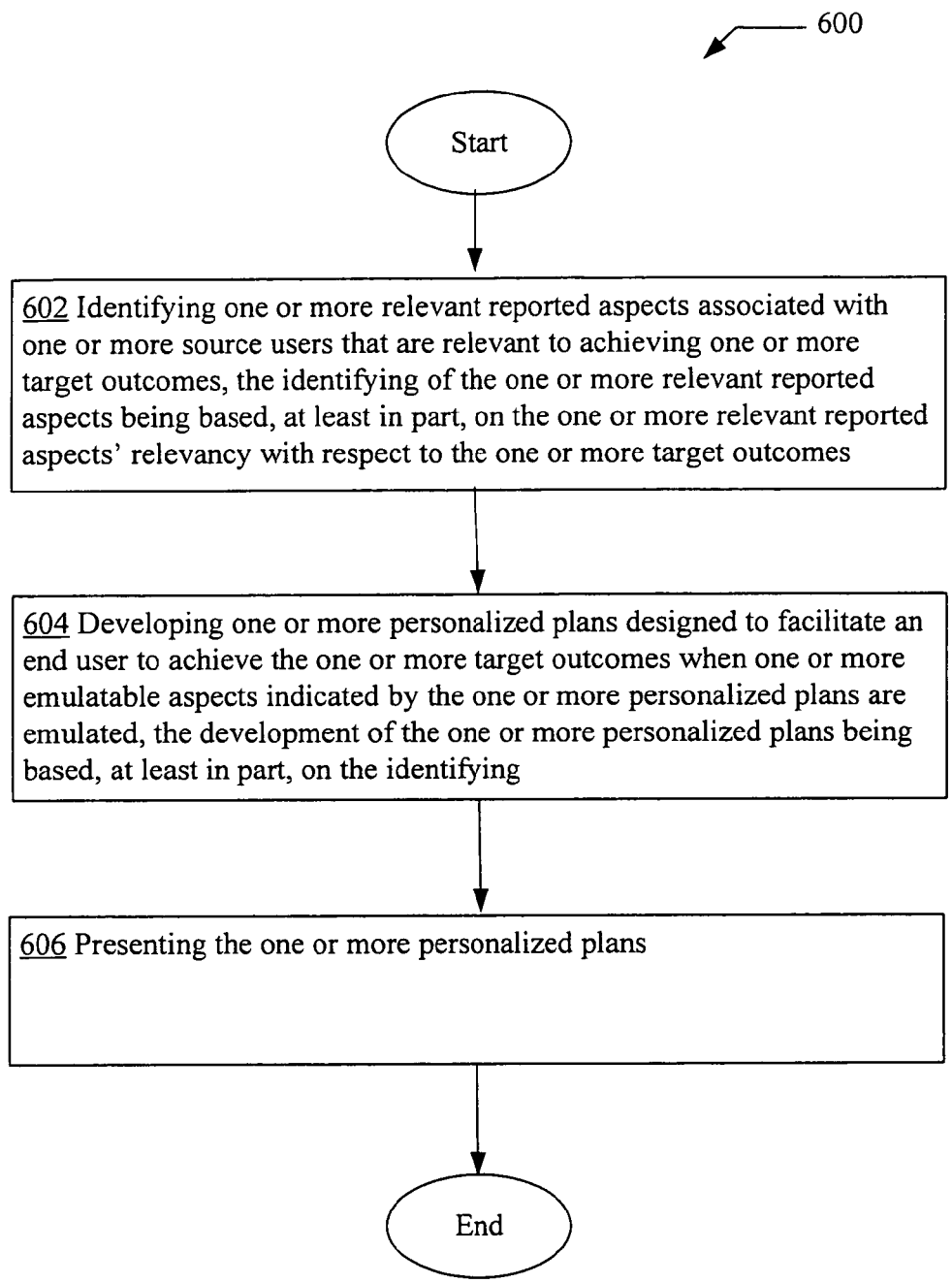
FIG. 6 is a high-level logic flowchart of another process.

Referring to FIG. 6 illustrating another operational flow 600 in accordance with various embodiments. Operational flow 600 includes certain operations that mirror the operations included in the operational flow 300 of FIG. 3. These operations include a relevant reported aspect identifying operation 602 and a personalized plan developing operation 604 that corresponds to and mirror the relevant reported aspect identifying operation 302 and the personalized plan developing operation 304, respectively, of FIG. 3.

In addition, operational flow 300 includes a personalized plan presenting operation 606 for presenting the one or more personalized plans as depicted in FIG. 6. For instance, the presentation module 106 of the computing device 10 presenting (e.g., transmitting via the wireless network and/or wired network 50 or indicating via a user interface 120) the one or more personalized plans 16.

Figure 7:
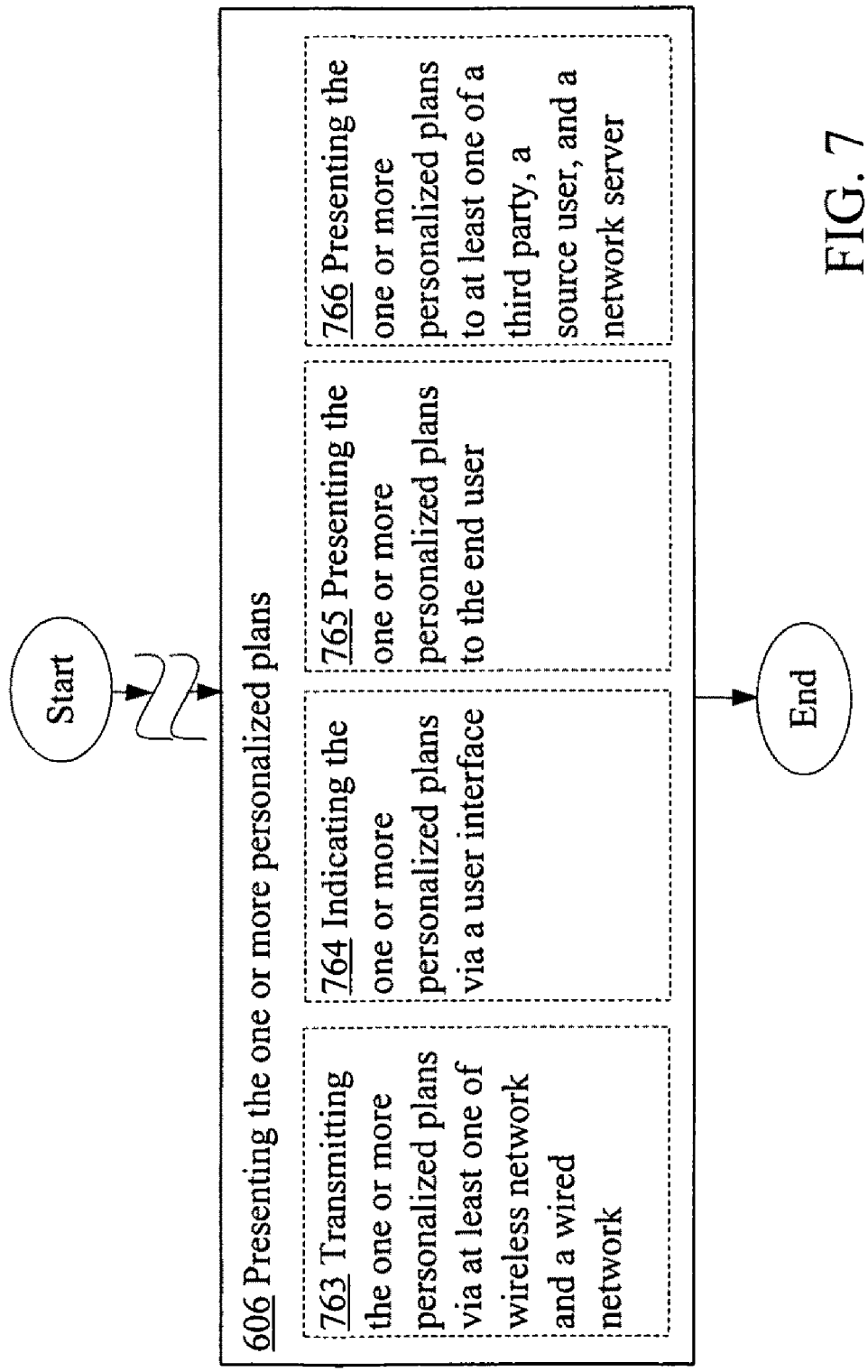
FIG. 7 is a high-level logic flowchart of a process depicting alternate implementations of the presentation operation 606 of FIG. 6.

In various alternative implementations, the personalized plan presenting operation 606 may include one or more additional operations. For example, in some implementations, the personalized plan presenting operation 606 may include an operation 763 for transmitting the one or more personalized plans via at least one of wireless network and a wired network as depicted in FIG. 7. For instance, the transmission module 224 of the computing device 10 transmitting the one or more personalized plans 16 via at least one of wireless network and a wired network 50.

In the same or different implementations, the personalized plan presenting operation 606 may include an operation 764 for indicating the one or more personalized plans via a user interface as depicted in FIG. 7. For instance, the user interface indication module 226 of the computing device 10 audioally and/or visually indicating the one or more personalized plans 16 via a user interface 120 (e.g., a display monitor, a touchscreen, an audio system including one or more speakers, and so forth).

In the same or different implementations, the personalized plan presenting operation 606 may include an operation 765 for presenting the one or more personalized plans to the end user as depicted in FIG. 7. For instance, the presentation module 106 of the computing device 10 presenting the one or more personalized plans 16 to the end user 4.

In the same or different implementations, the personalized plan presenting operation 606 may include an operation 766 for presenting the one or more personalized plans to at least one of a third party, a source user, and a network server as depicted in FIG. 7. For instance, the presentation module 106 of the computing device 10 presenting the one or more personalized plans 16 to at least one of a third party 6, a source user 2*, and a network server 60.

Figure 8:
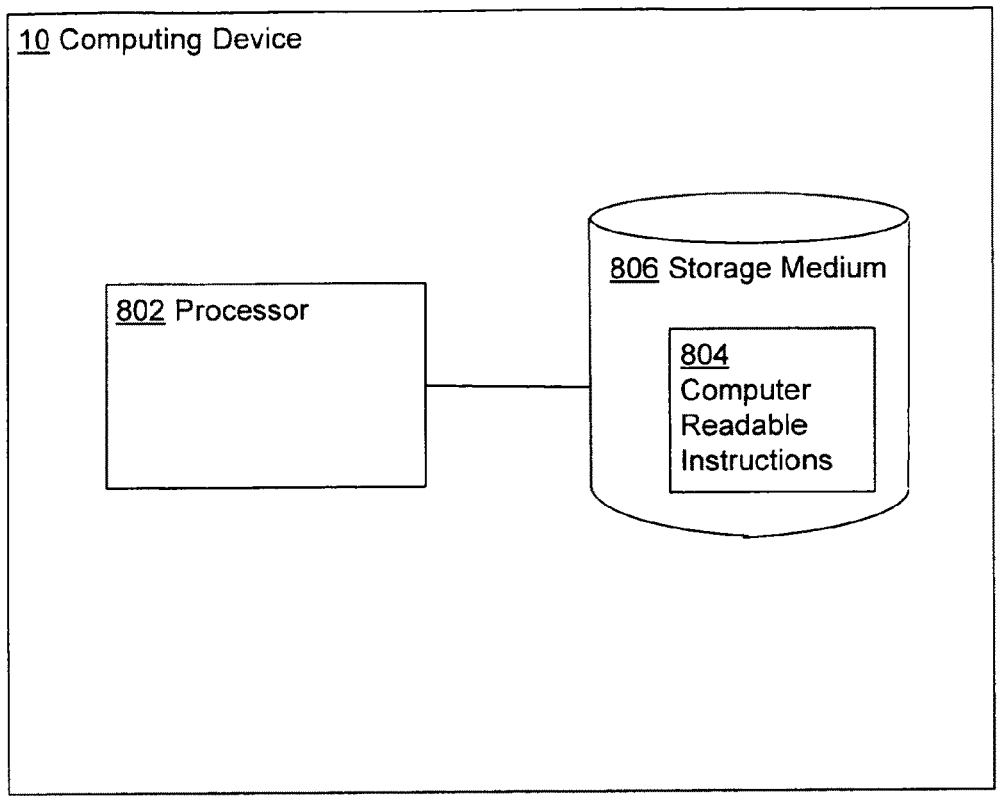
FIG. 8 is another high-level block diagram showing another perspective of the computing device 10 of FIG. 1b.

Turning now to FIG. 8, which is a high-level block diagram illustrating another perspective of the computing device 10 of FIG. 1b. As illustrated, the computing device 10 may include a processor 802 (e.g., microprocessor, controller, and so forth) coupled to storage medium 806 (e.g., volatile or non-volatile memory). The storage medium 806 may store computer readable instructions 804 (e.g., computer program product). The processor 802, in various implementations, may execute the computer readable instructions 804 in order to execute one or more operations described above and as illustrated in FIGS. 3, 4a, 4b, 4c, 4d, 4e, 4f, 4g, 4h, 5a, 5b, 5c, 5d, 6, and 7.

For example, the processor 802 may execute the computer readable instructions 804 in order to identify one or more relevant reported aspects associated with one or more source users 2 that are relevant to achieving one or more target outcomes, the identifying of the one or more relevant reported aspects being based, at least in part, on the one or more relevant reported aspects' relevancy with respect to the one or more target outcomes; and/or to develop one or more personalized plans 16 designed to facilitate an end user 4 to achieve the one or more target outcomes when one or more emulatable aspects indicated by the one or more personalized plans 16 are emulated, the development of the one or more personalized plans 16 being based, at least in part, on the identifying of the one or more relevant reported aspects as depicted in the operational flow 300 of FIG. 3.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system, comprising:
    a relevant reported aspect identification module configured to identify one or more relevant reported aspects based, at least in part, on the one or more relevant reported aspects' relevancy with respect to one or more target outcomes, the one or more relevant reported aspects to be identified being associated with one or more source users and being relevant to achieving the one or more target outcomes; and
    a personalized plan development module configured to develop one or more personalized plans based, at least in part, on the one or more relevant reported aspects, the one or more personalized plans to be developed being designed to facilitate an end user to achieve the one or more target outcomes when one or more emulatable aspects indicated by the one or more personalized plans are emulated, wherein said personalized plan development module, comprises:
        an emulatable aspect inclusion module configured to include one or more emulatable aspects that correspond to the one or more relevant reported aspects into each of the one or more personalized plans, wherein said personalized plan development module, comprises:
            a limitation compliance determination module configured to determine whether the one or more emulatable aspects to be included in the one or more personalized plans does not comply with one or more limitations associated with the end user, and if not compliant, execute one or more actions.

2. The system of claim 1, wherein said limitation compliance determination module, comprises:
    a non-compliance notification module configured to notify at least one of the end user and a third party regarding non-compliance of the one or more emulatable aspects in response to a determination of non-compliance with the one or more limitations.

3. The system of claim 1, wherein said limitation compliance determination module, comprises:
    a personalized plan modification module configured to modify the one or more personalized plans including replacing one or more emulatable aspects that have been determined not to be in compliance with the one or more limitations with one or more replacement emulatable aspects that complies with the one or more limitations.

4. The system of claim 1, wherein said limitation compliance determination module, comprises:
    a limitation compliance determination module configured to determine whether the one or more emulatable aspects to be included in the one or more personalized plans complies with at least one of a contextual, physical, personal, health, medical, user state, or legal limitation associated with the end user.

5. The system of claim 1, wherein said personalized plan development module, comprises:
    a personalized plan development module configured to develop at least one personalized plan that is designed to facilitate the end user to achieve one or more health or medical outcomes.

6. The system of claim 1, wherein said personalized plan development module, comprises:
    a personalized plan development module configured to develop at least one personalized plan that is designed to facilitate the end user to achieve one or more athletic outcomes.

7. The system of claim 1, wherein said personalized plan development module, comprises:
    a personalized plan development module configured to develop at least one personalized plan that is designed to facilitate the end user to achieve one or more occupational outcomes.

8. The system of claim 1, wherein said personalized plan development module, comprises:
    a personalized plan development module configured to develop at least one personalized plan that is designed to facilitate the end user to achieve one or more social outcomes.

9. The system of claim 1, wherein said personalized plan development module, comprises:
    a personalized plan development module configured to develop at least one personalized plan that is designed to facilitate the end user to achieve one or more psychological outcomes.

10. The system of claim 1, wherein said personalized plan development module, comprises:
    a personalized plan development module configured to develop at least one personalized plan that is designed to facilitate the end user to achieve one or more intellectual or academic outcomes.

11. The system of claim 1, wherein said personalized plan development module, comprises:
a personalized plan development module configured to develop at least one personalized plan that is designed to facilitate the end user to achieve one or more user states.

12. The system of claim 1, further comprising:
a presentation module configured to present the one or more personalized plans.

13. The system of claim 1, wherein said relevant reported aspect identification module, comprises:
a relevant reported aspect identification module configured to identify one or more reported aspects that are at least relevant for achieving the one or more target outcomes from a plurality of reported aspects.

14. The system of claim 13, wherein said relevant reported aspect identification module, comprises:
a source user associated reported aspect identification module configured to identify one or more reported aspects that are associated with the one or more source users from the plurality of reported aspects, the one or more source users having achieved the one or more target outcomes.

15. The system of claim 14, wherein said source user associated reported aspect identification module, comprises:
a target outcome corresponding reported aspect identification module configured to identify from the plurality of reported aspects one or more reported aspects that correspond to the one or more target outcomes.

16. The system of claim 15, wherein said source user associated reported aspect identification module, comprises:
an associated source user determination module configured to determine one or more source users who are associated with the one or more reported aspects that correspond to the one or more target outcomes.

17. The system of claim 16, wherein said source user associated reported aspect identification module, comprises:
a source user associated reported aspect identification module configured to identify one or more reported aspects that are associated with the determined one or more source users.

18. The system of claim 17, wherein said relevant reported aspect identification module, comprises:
a relevancy factor relevant reported aspect identification module configured to identify, from the one or more reported aspects that are associated with the determined one or more source users, one or more reported aspects that are relevant with respect to one or more relevancy factors.

19. The system of claim 18, wherein said relevancy factor relevant reported aspect identification module, comprises:
a relevancy factor relevant reported aspect identification module configured to identify one or more reported aspects that belong to one or more aspect types that are of interest to the end user.

20. The system of claim 18, wherein said relevancy factor relevant reported aspect identification module, comprises:
a relevancy factor relevant reported aspect identification module configured to identify one or more reported aspects that belong to one or more aspect types that have been indicated by at least one source user as being relevant to the achievement of the one or more target outcomes.

21. The system of claim 18, wherein said relevancy factor relevant reported aspect identification module, comprises:
a relevancy factor relevant reported aspect identification module configured to identify one or more reported aspects that belong to one or more aspect types that have been indicated by at least one third party source as being relevant to the achievement of the one or more target outcomes.

22. The system of claim 18, wherein said relevancy factor relevant reported aspect identification module, comprises:
a relevancy factor relevant reported aspect identification module configured to identify one or more reported aspects that indicate one or more aspects that occurred within one or more predefined time periods, respectively, from one or more occurrences of the one or more reported aspects that correspond to the one or more target outcomes.

23. The system of claim 22, wherein said relevancy factor relevant reported aspect identification module, comprises:
a relevancy factor relevant reported aspect identification module configured to identify one or more reported aspects that indicate one or more aspects that occurred prior to and within one or more predefined time periods, respectively, from one or more occurrences of the one or more reported aspects that correspond to the one or more target outcomes.

24. The system of claim 1, wherein said relevant reported aspect identification module, comprises:
a relevancy factor relevant reported aspect identification module configured to at least identify one or more reported aspects that are relevant with respect to one or more relevancy factors.

25. The system of claim 1, wherein said relevant reported aspect identification module, comprises:
a relevant reported aspect identification module configured to identify one or more relevant reported aspects that were at least originally reported via one or more log entries.

26. The system of claim 25, wherein said relevant reported aspect identification module, comprises:
a relevant reported aspect identification module configured to identify one or more relevant reported aspects that were at least originally reported via one or more blog entries.

27. The system of claim 25, wherein said relevant reported aspect identification module, comprises:
a relevant reported aspect identification module configured to identify one or more relevant reported aspects that were at least originally reported via one or more status reports.

28. The system of claim 25, wherein said relevant reported aspect identification module, comprises:
a relevant reported aspect identification module configured to identify one or more relevant reported aspects that were at least originally reported via one or more log entries as provided by one or more sensing devices.

29. The system of claim 1, wherein said relevant reported aspect identification module, comprises:
a relevant reported aspect identification module configured to identify a first one or more reported aspects that are associated with a first source user and that are relevant to achieving a first one or more target outcomes and identifying a second one or more reported aspects that are associated with a second source user and that are relevant to achieving a second one or more target outcomes, the identifying of the first one or more reported aspects being based on the first one or more reported aspects' relevancy with respect to the first one or more target outcomes and the identifying of the second one or more reported aspects being based on the second one or more reported aspects' relevancy with respect to the second one or more target outcomes.

30. The system of claim 1, wherein said relevant reported aspect identification module, comprises:
- a relevant reported aspect identification module configured to identify a first one or more reported aspects that are associated with a first source user and that are relevant to achieving at least one target outcome and identifying a second one or more reported aspects that are associated with a second source user and that are relevant to achieving the at least one target outcome, the identifying of the first one or more reported aspects and the second one or more reported aspects being based on the first one or more reported aspects' and the second one or more reported aspects' relevancy with respect to the at least one target outcome.

31. The system of claim 1, wherein said relevant reported aspect identification module, comprises:
- a relevant reported aspect identification module configured to identify one or more relevant reported aspects that are related to one or more behavior incidences associated with the one or more source users.

32. The system of claim 1, wherein said relevant reported aspect identification module, comprises:
- a relevant reported aspect identification module configured to identify one or more relevant reported aspects that are related to one or more incidences of one or more user beliefs associated with the one or more source users.

33. The system of claim 1, wherein said relevant reported aspect identification module, comprises:
- a relevant reported aspect identification module configured to identify one or more relevant reported aspects that are related to one or more incidences of one or more subjective user states associated with the one or more source users.

34. The system of claim 1, wherein said relevant reported aspect identification module, comprises:
- a relevant reported aspect identification module configured to identify one or more relevant reported aspects that are related to one or more incidences of one or more user physical characteristics associated with the one or more source users.

35. The system of claim 1, wherein said relevant reported aspect identification module, comprises:
- a relevant reported aspect identification module configured to identify one or more relevant reported aspects that are related to one or more incidences of user locations associated with the one or more source users.

36. The system of claim 1, wherein said relevant reported aspect identification module, comprises:
- a relevant reported aspect identification module configured to identify one or more relevant reported aspects that are related to one or more incidences of external events associated with the one or more source users.

37. The system of claim 1, wherein said emulatable aspect inclusion module, comprises:
- an emulatable aspect inclusion module configured to include a plurality of emulatable aspects that corresponds to a plurality of relevant reported aspects that are associated with the one or more source users and that are relevant to achieving the one or more target outcomes into each of the one or more personalized plans.

38. The system of claim 37, wherein said personalized plan development module, comprises:
- a relationship defining module configured to define one or more relationships between the plurality of emulatable aspects included in each of the one or more personalized plans in each of the one or more personalized plans.

39. A system, comprising:
- a relevant reported aspect identification module configured to identify one or more relevant reported aspects based, at least in part, on the one or more relevant reported aspects' relevancy with respect to one or more target outcomes, the one or more relevant reported aspects to be identified being associated with one or more source users and being relevant to achieving the one or more target outcomes; and
- a personalized plan development module configured to develop one or more personalized plans based, at least in part, on the one or more relevant reported aspects, the one or more personalized plans to be developed being designed to facilitate an end user to achieve the one or more target outcomes when one or more emulatable aspects indicated by the one or more personalized plans are emulated, wherein said personalized plan development module, comprises:
  - an emulatable aspect inclusion module configured to include one or more emulatable aspects that correspond to the one or more relevant reported aspects into each of the one or more personalized plans, wherein said personalized plan development module, comprises:
    - a plausible determination module configured to determine whether at least one of the one or more emulatable aspects to be included in the one or more personalized plans is a plausible aspect that has been successfully emulated by one or more third parties, and if not a plausible aspect, execute one or more actions.

40. The system of claim 39, wherein said plausible determination module, comprises:
- a not plausible notification module configured to notify at least one of the end user and a third party regarding determination that the at least one of the one or more emulatable aspects to be included in the one or more personalized plans is not a plausible aspect in response to determining that the at least one of the one or more emulatable aspects to be included in the one or more personalized plans is not a plausible aspect.

41. The system of claim 39, wherein said plausible determination module, comprises:
- a personalized plan modification module configured to modify, at least one of the one or more personalized plans by replacing the at least one of the one or more emulatable aspects determined to be not a plausible aspect with at least one replacement emulatable aspect that is a plausible aspect that has been successfully emulated by one or more third parties in response to determining that the at least one of the one or more emulatable aspects is not a plausible aspect.

42. The system of claim 39, wherein said plausible determination module, comprises:
- a plausible determination module configured to determine whether at least one of the one or more emulatable aspects to be included in the one or more personalized plans is a plausible aspect that has been successfully emulated by the one or more third parties in order to achieve at least one of the one or more target outcomes, and if not a plausible aspect, execute the one or more actions.

43. A system, comprising:
- circuitry for identifying one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes; and circuitry for developing one or more personalized plans designed to facilitate an end user to achieve the one or more target outcomes when one or more emulatable aspects indicated by the one or more personalized plans are emulated, the development of the one or more personalized plans being based, at least in part, on the identifying, wherein said circuitry for developing one or more personalized plans designed to facilitate an end user to achieve the one or more target outcomes when one or more emulatable aspects indicated by the one or more personalized plans are emulated, the development of the one or more personalized plans being based, at least in part, on the identifying comprises:

circuitry for including into each of the one or more personalized plans one or more emulatable aspects that correspond to the one or more relevant reported aspects, wherein said circuitry for including into each of the one or more personalized plans one or more emulatable aspects that correspond to the one or more relevant reported aspects comprises:

circuitry for determining whether the one or more emulatable aspects to be included in the one or more personalized plans complies with one or more limitations associated with the end user, and if not, execute one or more actions.

44. An article of manufacture, comprising:

a non-transitory storage medium bearing:

one or more instructions for identifying one or more relevant reported aspects associated with one or more source users that are relevant to achieving one or more target outcomes, the identifying of the one or more relevant reported aspects being based, at least in part, on the one or more relevant reported aspects' relevancy with respect to the one or more target outcomes; and one or more instructions for developing one or more personalized plans designed to facilitate an end user to achieve the one or more target outcomes when one or more emulatable aspects indicated by the one or more personalized plans are emulated, the development of the one or more personalized plans being based, at least in part, on the identifying, wherein said one or more instructions for developing one or more personalized plans designed to facilitate an end user to achieve the one or more target outcomes when one or more emulatable aspects indicated by the one or more personalized plans are emulated, the development of the one or more personalized plans being based, at least in part, on the identifying comprises:

one or more instructions for including into each of the one or more personalized plans one or more emulatable aspects that correspond to the one or more relevant reported aspects, wherein said one or more instructions for including into each of the one or more personalized plans one or more emulatable aspects that correspond to the one or more relevant reported aspects comprises:

one or more instructions for determining whether the one or more emulatable aspects to be included in the one or more personalized plans complies with one or more limitations associated with the end user, and if not, execute one or more actions.

\* \* \* \* \*